United States Patent [19]

Kanno et al.

[11] Patent Number: 5,111,306
[45] Date of Patent: May 5, 1992

[54] ENDOSCOPE IMAGE FILING SYSTEM

[75] Inventors: Masahide Kanno, Hachioji; Shouichi Ieoka, Takahama; Keiichi Hiyama, Akishima; Kenji Matsunaka; Tadao Eto, both of Hachioji, all of Japan

[73] Assignee: Olympus Optical Co., Ltd., Tokyo, Japan

[21] Appl. No.: 685,793

[22] Filed: Apr. 16, 1991

[30] Foreign Application Priority Data

Apr. 18, 1990 [JP] Japan .................. 2-102386

[51] Int. Cl.$^5$ .......................... H04N 7/18; A61B 9/06
[52] U.S. Cl. ...................................... 358/403; 128/6; 358/98; 358/448; 358/462; 358/426
[58] Field of Search ................. 358/98, 403, 426, 448, 358/462; 128/6

[56] References Cited

U.S. PATENT DOCUMENTS

| 4,607,290 | 8/1986 | Murakami | 358/426 |
|---|---|---|---|
| 4,727,417 | 2/1988 | Kanno et al. | 358/98 |
| 4,768,099 | 8/1988 | Mukai | 358/426 |
| 4,920,413 | 4/1990 | Nakamura | 358/98 |
| 5,029,016 | 7/1991 | Hiyama | 358/98 |
| 5,031,036 | 7/1991 | Kikuchi | 358/98 |
| 5,061,994 | 10/1991 | Takahashi | 358/98 |

FOREIGN PATENT DOCUMENTS 63-153957  6/1988  Japan .

Primary Examiner—Howard W. Britton
Attorney, Agent, or Firm—Armstrong & Kubovcik

[57] ABSTRACT

An endoscope image filing apparatus wherein endoscope image information and search information required to search this image information are recorded in the same medium by a recording apparatus, on the other hand, medium discriminating information is imparted to this medium by an imparting apparatus and the search information and medium discriminating information are memorized in a controlling apparatus so that, in case there are many recording media, when the search information is input into the controlling apparatus, the medium discriminating information of the medium in which the search information is recorded may be obtained.

24 Claims, 20 Drawing Sheets

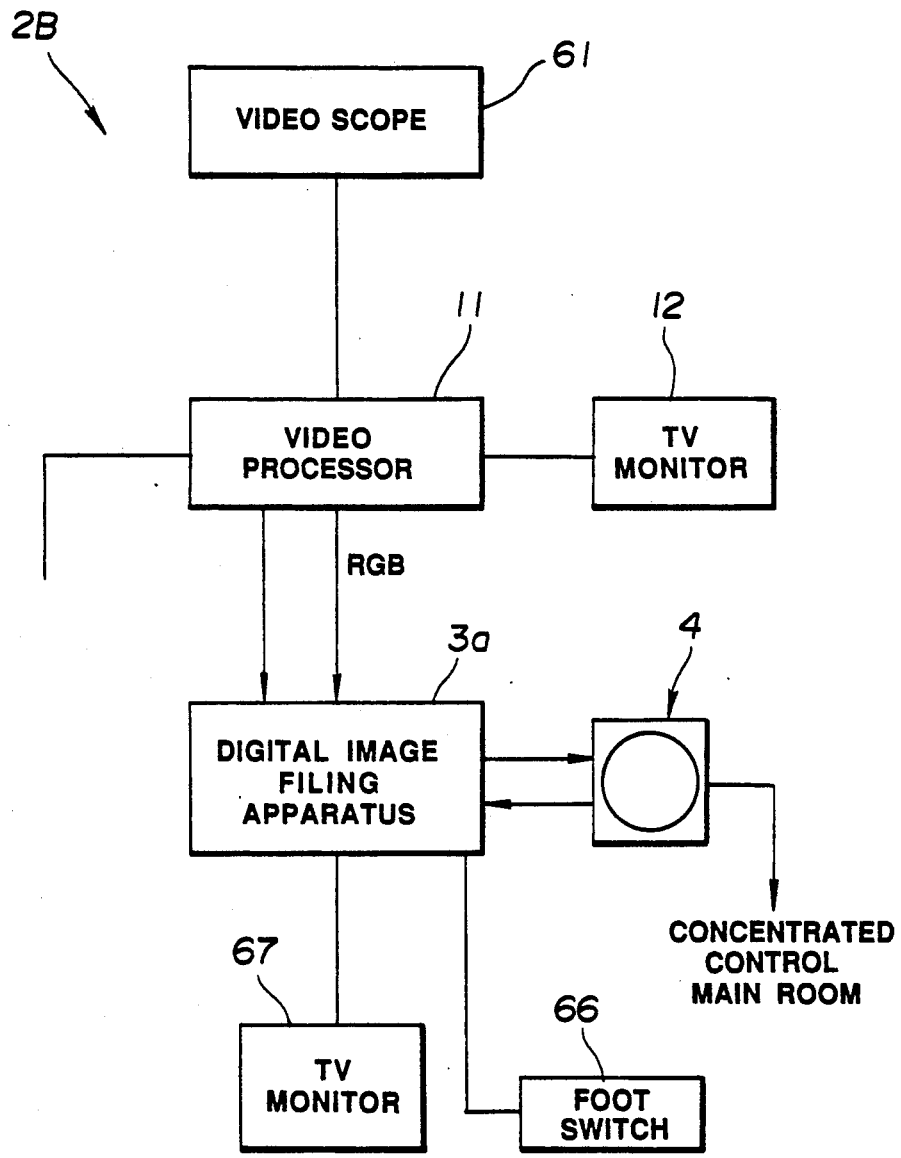

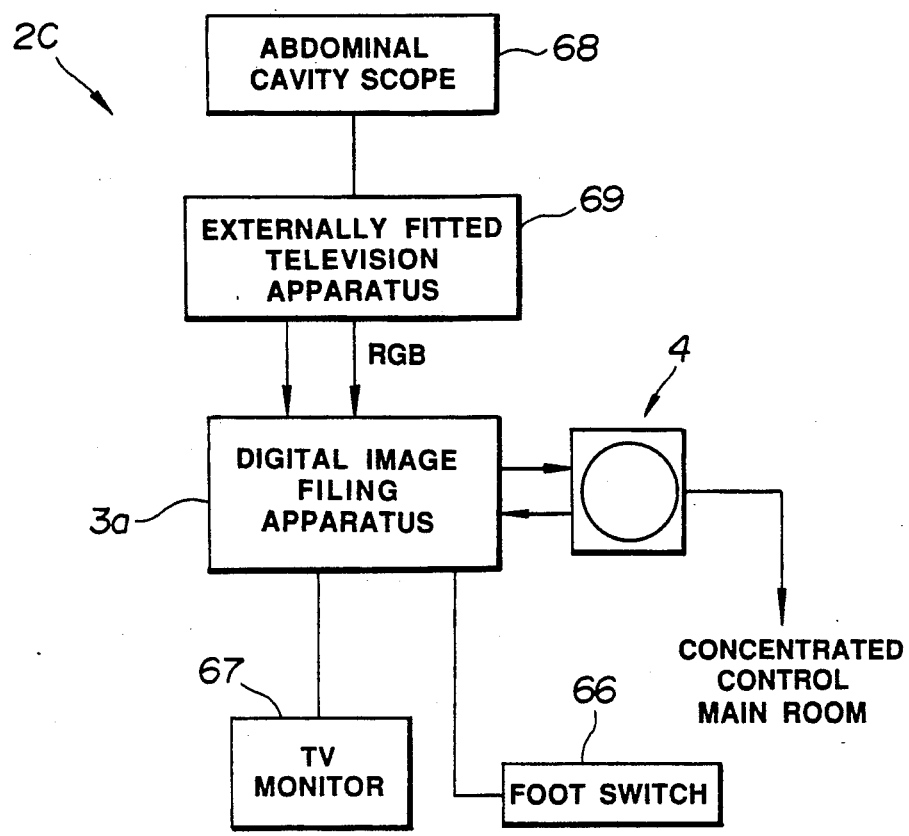
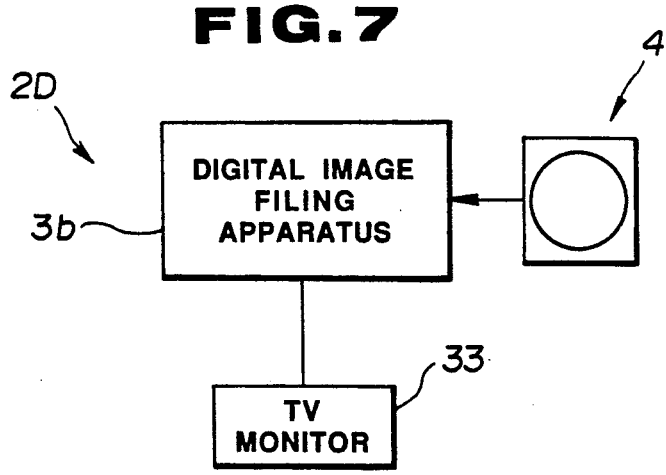

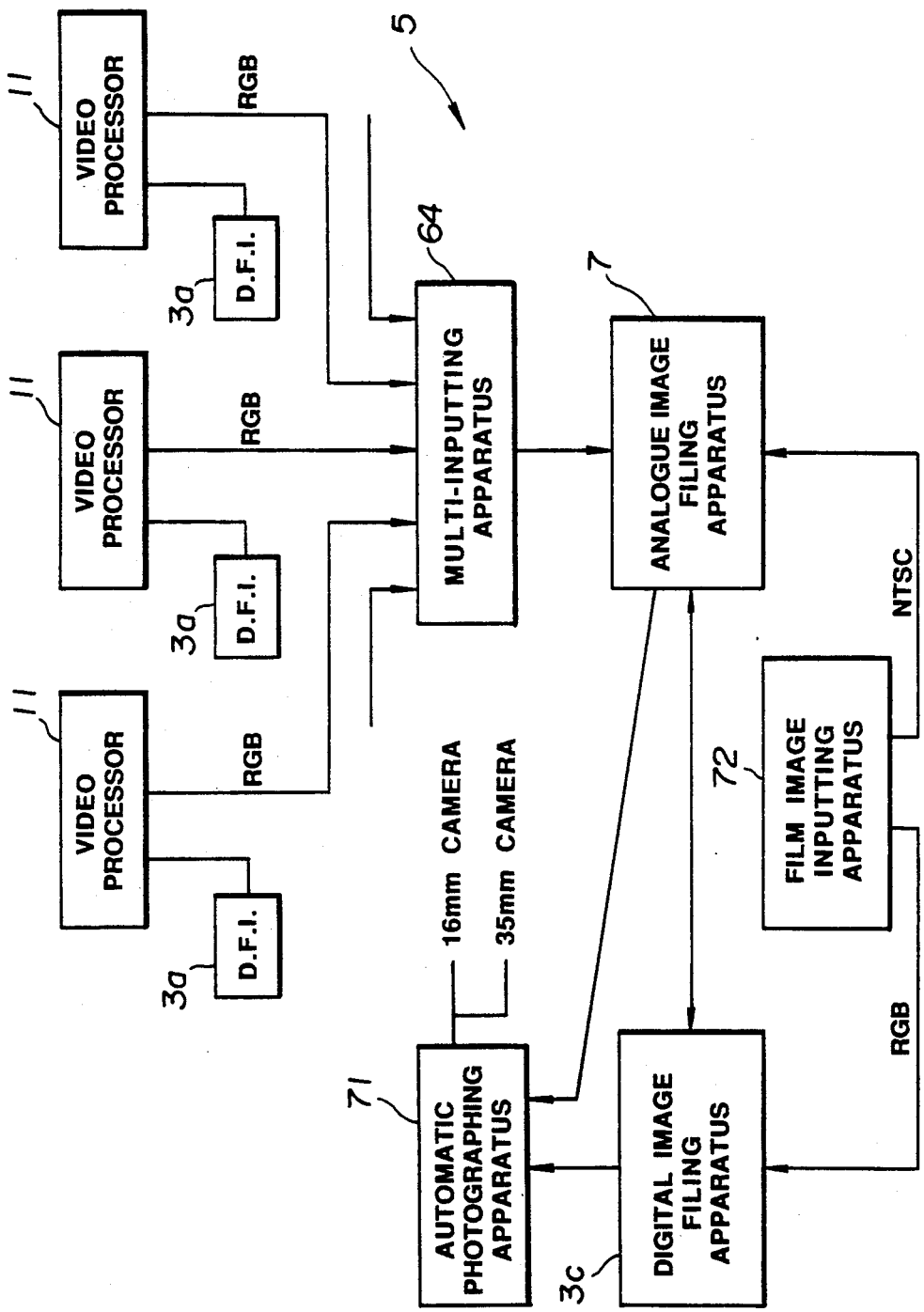

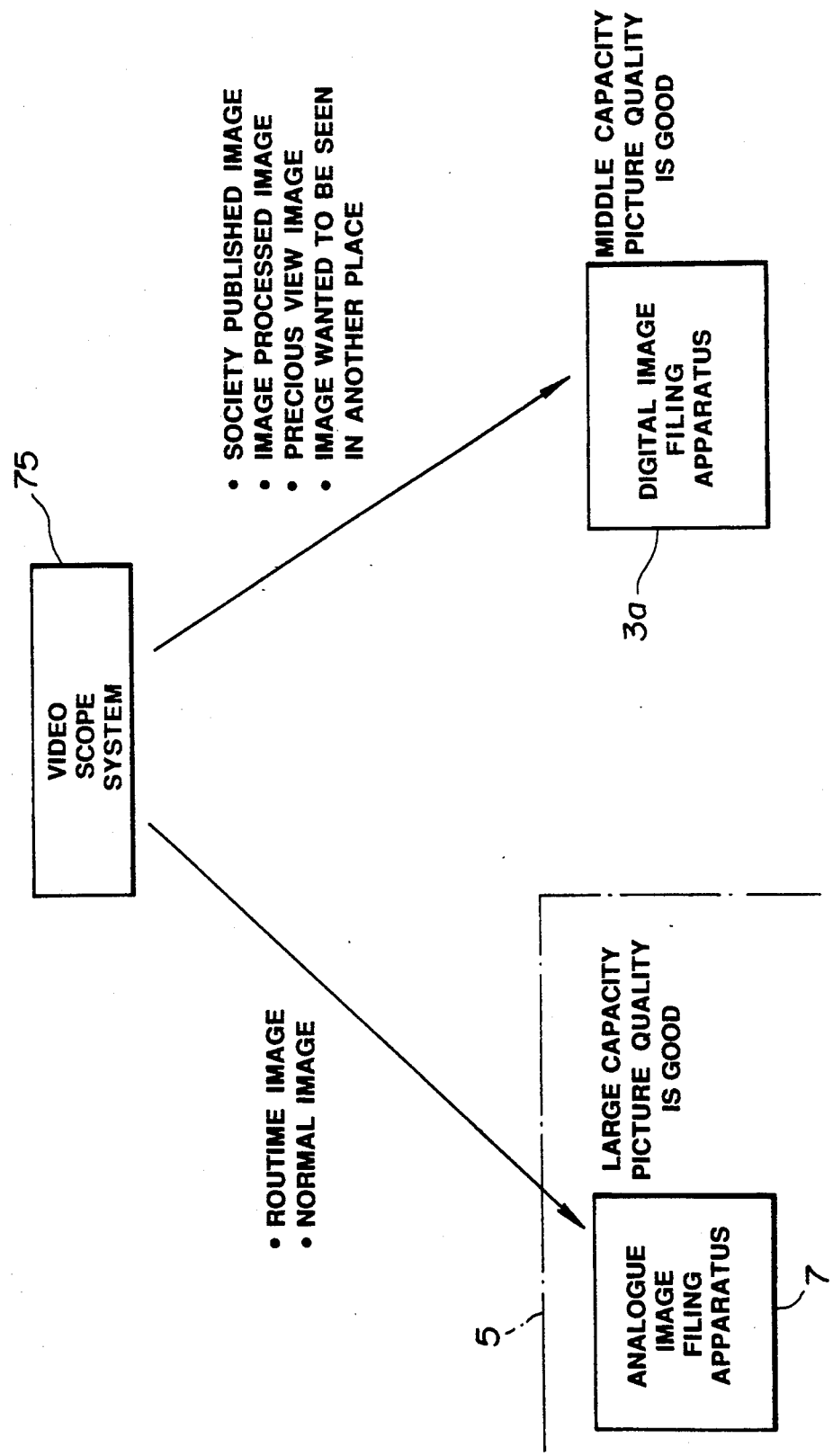

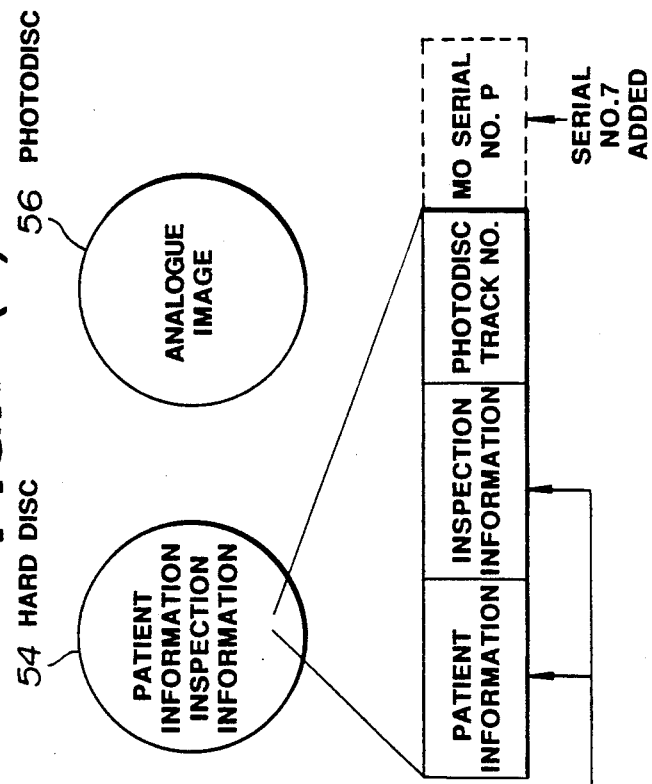
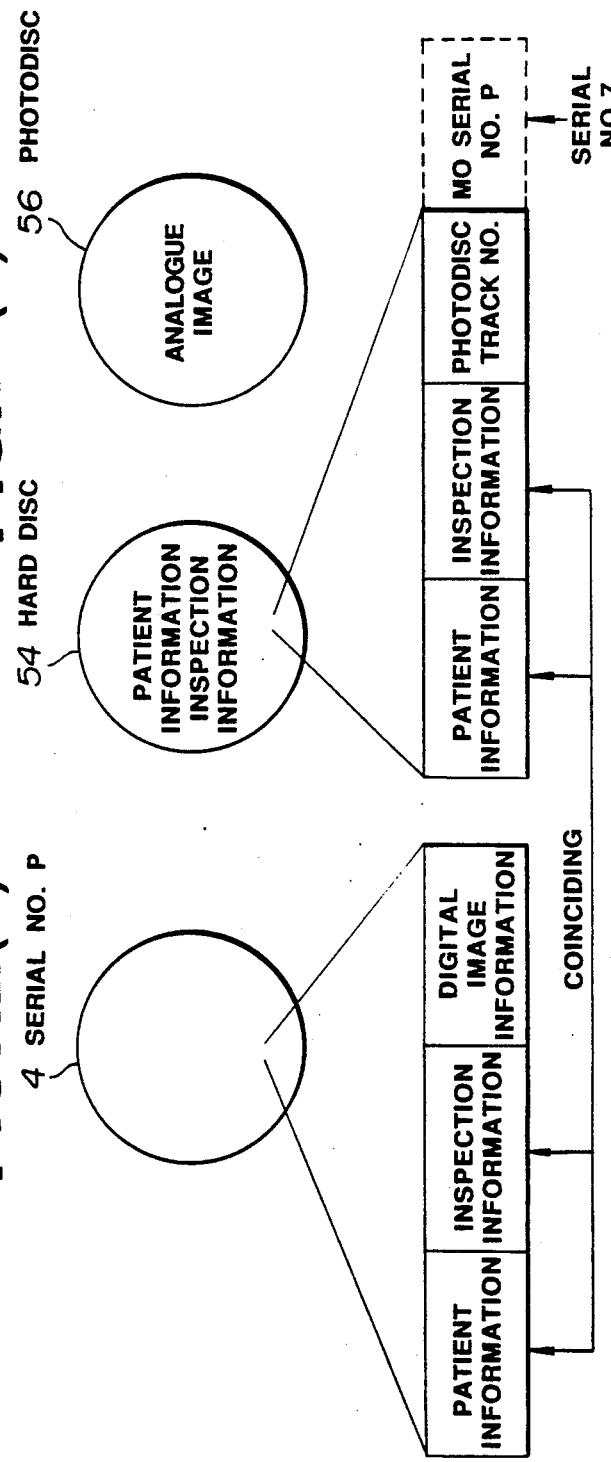

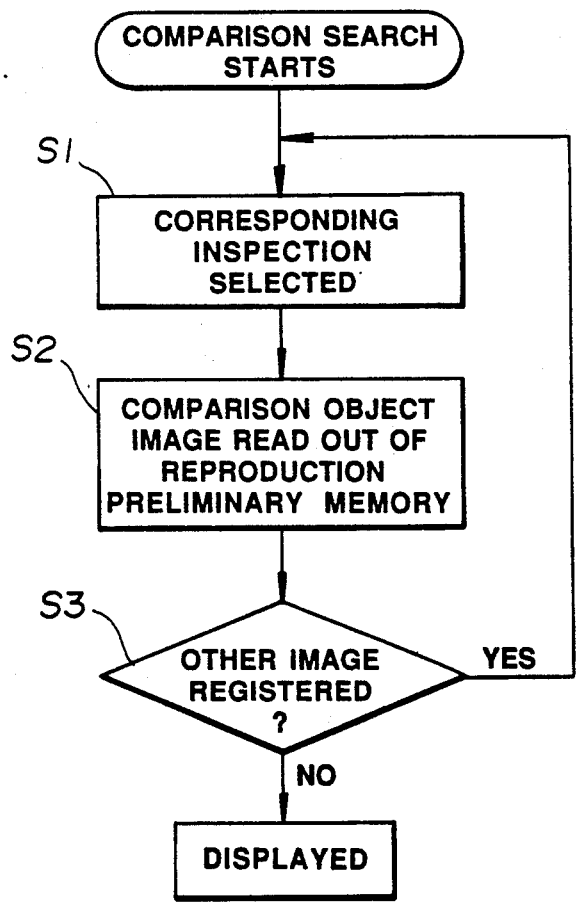

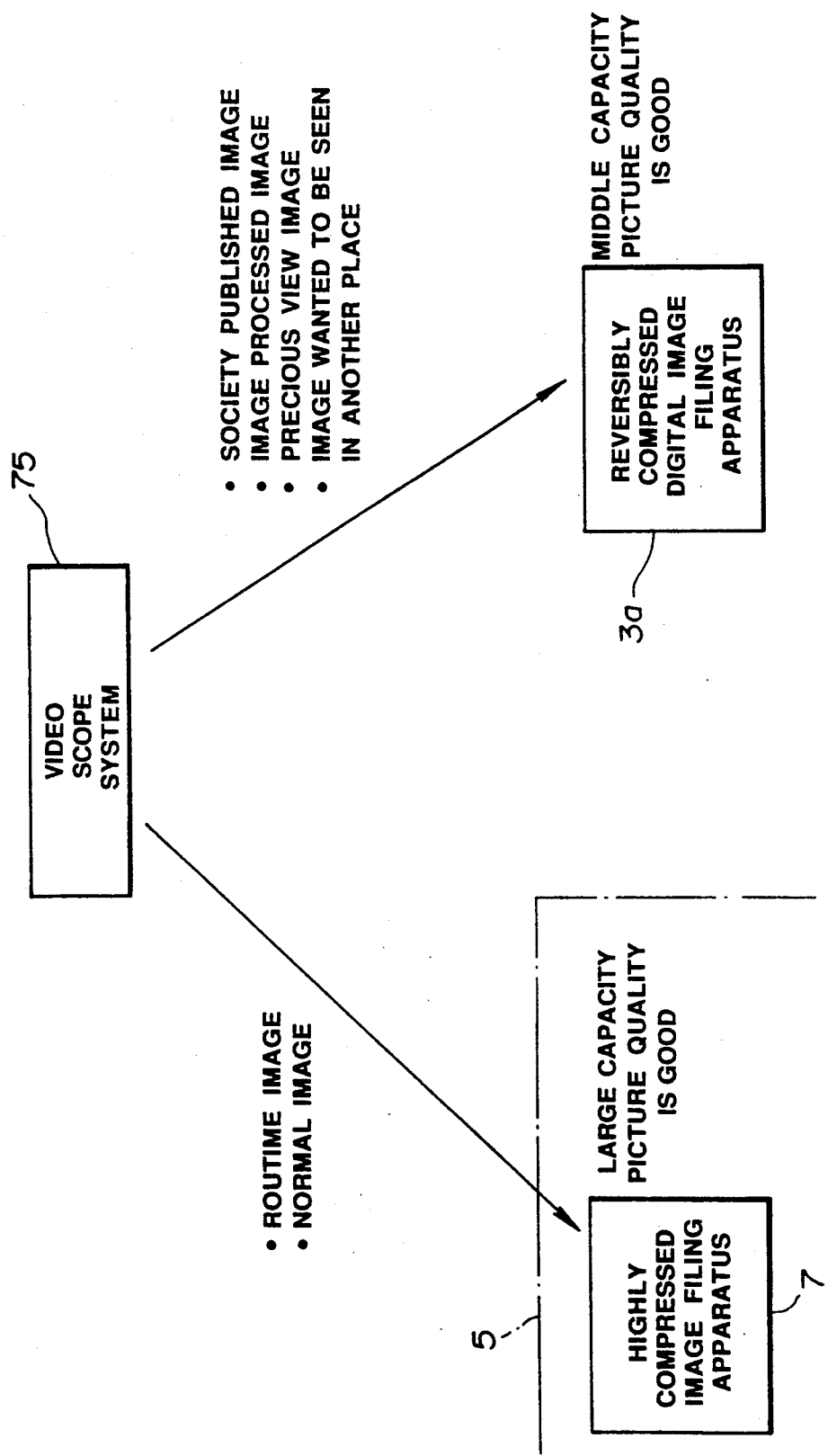

202
1/10 COMPRESSION RATE DISPLAYING LED    1/3 COMPRESSION RATE DISPLAYING LED

1/10 COMPRESSION SELECTING SW    1/3 COMPRESSION SELECTING SW
201

ENDOSCOPE IMAGE FILING SYSTEM

BACKGROUND OF THE INVENTION

1. Field of the Invention

This invention relates to an endoscope image filing system adapted to control recording media en bloc when there are many recording media and image filing apparatus.

2. Related Art Statement

Recently, there is extensively used an endoscope apparatus whereby organs within a body cavity can be observed, examined or diagnosed with a monitor picture by using such imaging means as a solid state imaging device.

In such endoscope apparatus, an endoscope image imaged by an electronic endoscope or the like is recorded in such recording medium as a photomagnetic disc or the like and is used as systematized by connecting image filing apparatus so as to be effectively utilized for a later diagnosis or the like and the system is desired to be easy to use.

In Japanese patent application laid open No.153957/1988 as the first related art example in this kind of system is suggested a system in which an analogue image filing apparatus and digital image filing apparatus can be commonly used. According to this related art, for example, an image high in the importance can be recorded in the digital image filing apparatus and an image low in the importance can be recorded in the analogue image filing apparatus.

Also, in Japanese patent application laid open No.115981/1990 as the second related art exaple is suggested a system in which an analogue image filing apparatus and digital image filing apparatus can be commonly used in the same manner and the recording destination of either of both filing apparatus can be selected from an endoscope apparatus.

Further, in Japanese patent application No.10228/1990 as the third related art example is suggested a system in which a photomagnetic disc in which an image is recorded digitally in an endoscope inspection room is conveyed to a conference room located in a separate place and the image can be read out.

Now, in the above mentioned first and second related art examples, in the system, for one image inputting apparatus, there are each of a digital image filing apparatus and analogue image filing apparatus and a file controller controlling them but there is no counter-measure on the control of data when data are exchanged among a plurality of systems, for example, when another set system coexists.

Therefore, in case a plurality of systems coexist, even if it is intended, for example, to search a former endoscope image to make it a reference for a diagnosis, as the image information is not integrally controlled among the respective systems, the endoscope image will not be able to be efficiently searched.

In the third related art example, it is, described that a photomagnetic disc recorded in an inspection room is conveyed to a separate room, for example, a conference room where the image can be read out. However, no counter-measure is made on the control of photomagnetic discs when the number of inspections increases so much that many photomagnetic discs exist.

Therefore, in case an endoscope image, for example, on a patient is to be searched, in what photomagnetic disc this image is recorded will not be known and therefore will have to be investigated by fitting, for example, respective photomagnetic discs as recording media to an image filing apparatus That is to say, in the above described respective related arts, particularly in case many of such recording media as photomagnetic discs are present, as they are not controlled en bloc, the system will not be easy to use.

OBJECTS AND SUMMARY OF THE INVENTION

An object of this invention is to provide an endoscope image filing system for controlling recording media en bloc so as to be easy to use in case many recording media are present.

Another object of this invention is to provide an endoscope image filing system whereby, in case many recording media are present, search information and medium discriminating information will be imparted to these recording media, the medium discriminating information and search information of these recording media will be controlled and the above mentioned search information will be input so that the medium, discriminating information of the media in which the search information is recorded may be obtained.

Further, another object of this invention is to provide an endoscope image filing system whereby endoscope image data obtained by an endoscope apparatus can be recorded by a digital image filing apparatus as digital image data in recording media and, on the other hand, can be recorded by an analogue image filing apparatus as analogue image data in recording media.

Furthermore, another object of this invention is to provide a endoscope image filing apparatus whereby recording media having recorded endoscope image information and search information required to search the endoscope image information can be conveyed to be set in image filing apparatus in respective places and can be reproduced and searched and the increase of satellite rooms or conference rooms can be easily coped with.

The endoscope image filing apparatus of this invention comprises a recording means for recording in the same medium endoscope image information ..and search information required to search the endoscope image information, a medium discriminating information imparting means for imparting medium discriminating information to the above mentioned medium, a medium controlling means for memorizing the above mentioned search information and the medium discriminating information of the medium in which this search information is recorded and a searching means for searching the medium discriminating information by inputting the above mentioned search information into the medium controlling means.

The other features and advantages of this invention will become apparent enough with the following explanation.

BRIEF DESCRIPTION OF THE DRAWINGS

FIGS. 1 to 13 relate to the first embodiment of the present invention.

FIG. 1 is a schematic view of the whole of the first embodiment.

FIG. 2 is a formation diagram of a digital image filing apparatus set in each of a satellite room and conference room.

FIG. 3 is a formation diagram of a digital and analogue image filing apparatus provided in a concentrated control main room.

FIG. 4 is a block diagram showing system component devices within an endoscope inspection satellite room.

FIG. 5 is a block diagram showing system component devices within an X-ray satellite room FIG. 6 is a block diagram showing system component devices within an operation satellite room.

FIG. 7 is a block diagram showing system component devices within a conference room.

FIG. 8 is a block diagram showing system component devices within a concentrated control main room.

FIG. 9 is an explanatory diagram of a general reference as to recording an endoscope image in an analogue image or digital image.

FIG. 10 is an explanatory view of information contents to be recorded in a photomagnetic disc.

FIG. 11 is a flow chart showing the contents of a registering operation.

FIG. 12 is an operation explaining diagram of FIG. 11.

FIG. 13 is an explanatory view showing the contents displayed in a display in the case of searching.

FIGS. 14 and 15 relate to a modification of the present invention.

FIG. 14 is a block diagram showing the system formation within the concentrated control main room.

FIG. 15 is an explanatory view of the case of recording an endoscope image in an analogue image and digital image.

FIG. 16 is a schematic view showing the whole of the second embodiment.

FIG. 17 is a formation diagram of a digital and analogue image filing apparatus provided in the concentrated control main room.

FIGS. 18 to 20 relate to the third embodiment of the present invention.

FIG. 18 is a formation diagram of a digital image filing apparatus provided in a conference room in the third embodiment.

FIG. 19 is a flow chart showing the contents displaying original images selected from contracted images.

FIG. 20 is an explanatory view showing the display of contracted images and the display of selected original images.

DETAILED DESCRIPTION OF THE PREFERRED EMBODIMENTS

Figure 1:
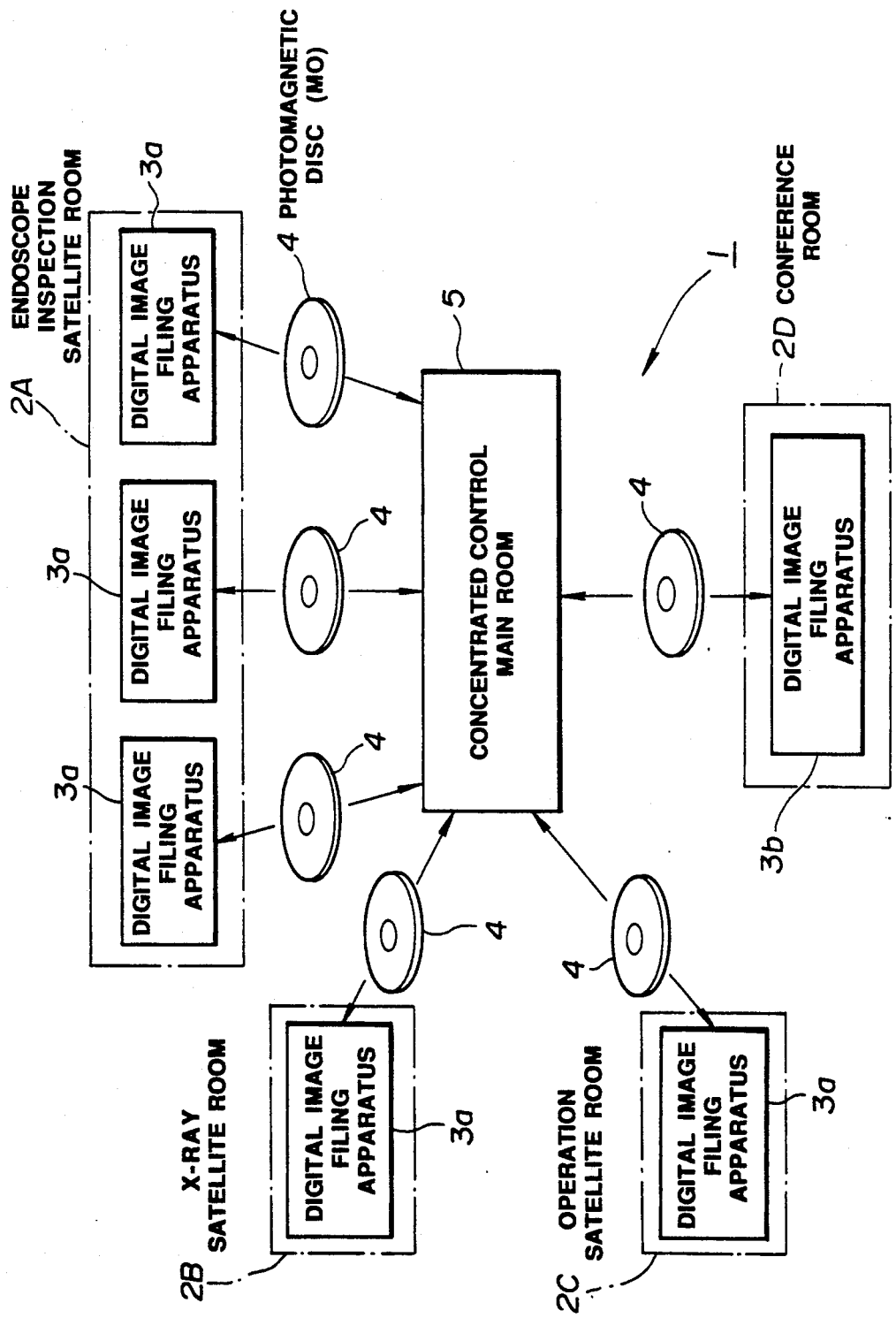

As shown in FIG. 1, in an endoscope image filing system 1 of the first embodiment, photomagnetic discs 4 in which endoscope images are recorded together with their search information in digital image filing apparatus 3a which are present respectively in such satellite rooms, for example, in a hospital or the like as, for example, an endoscope inspection satellite room 2A, X-ray satellite room 2B and operation satellite room 2C and photomagnetic discs (briefly mentioned as MO's hereinafter) in which images are read out by a digital image filing apparatus 3b provided in a conference room 2D are controlled en bloc or concentrated and controlled.

Figure 3:
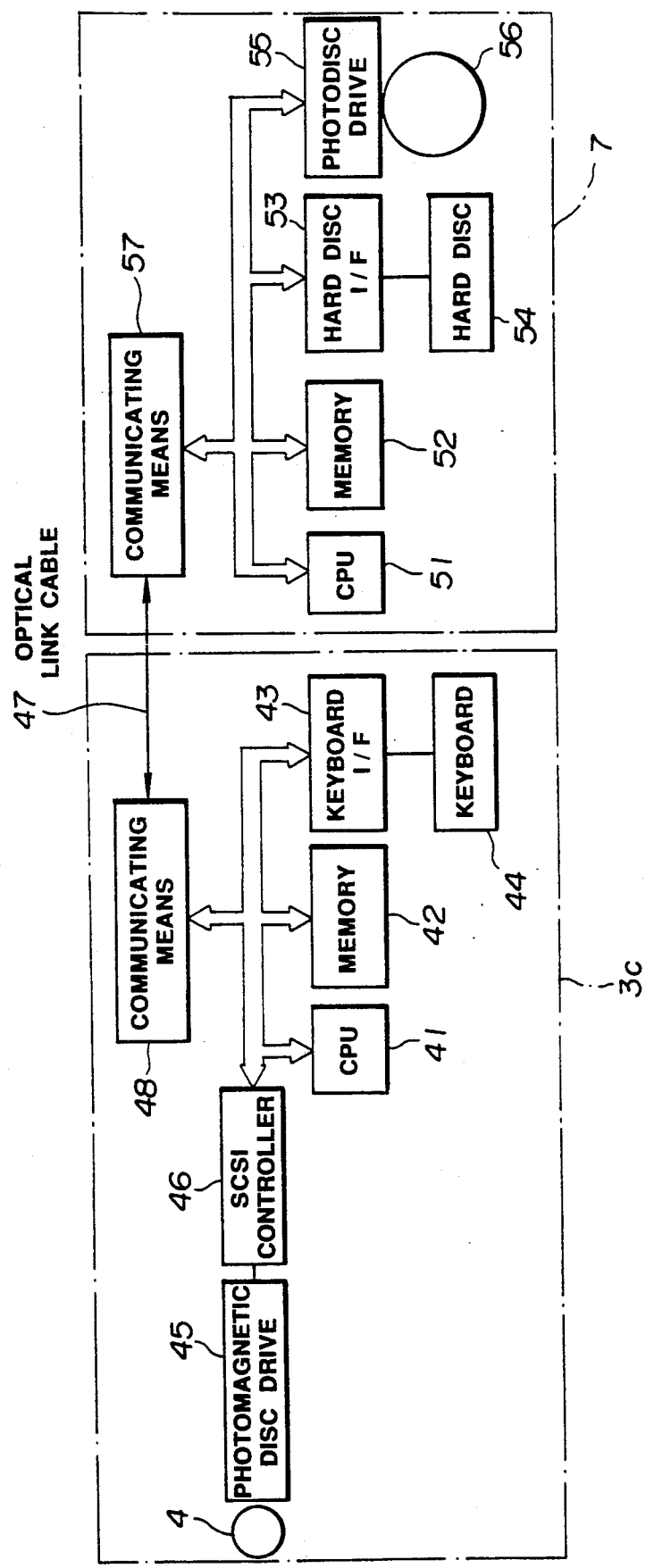
Figure 4:
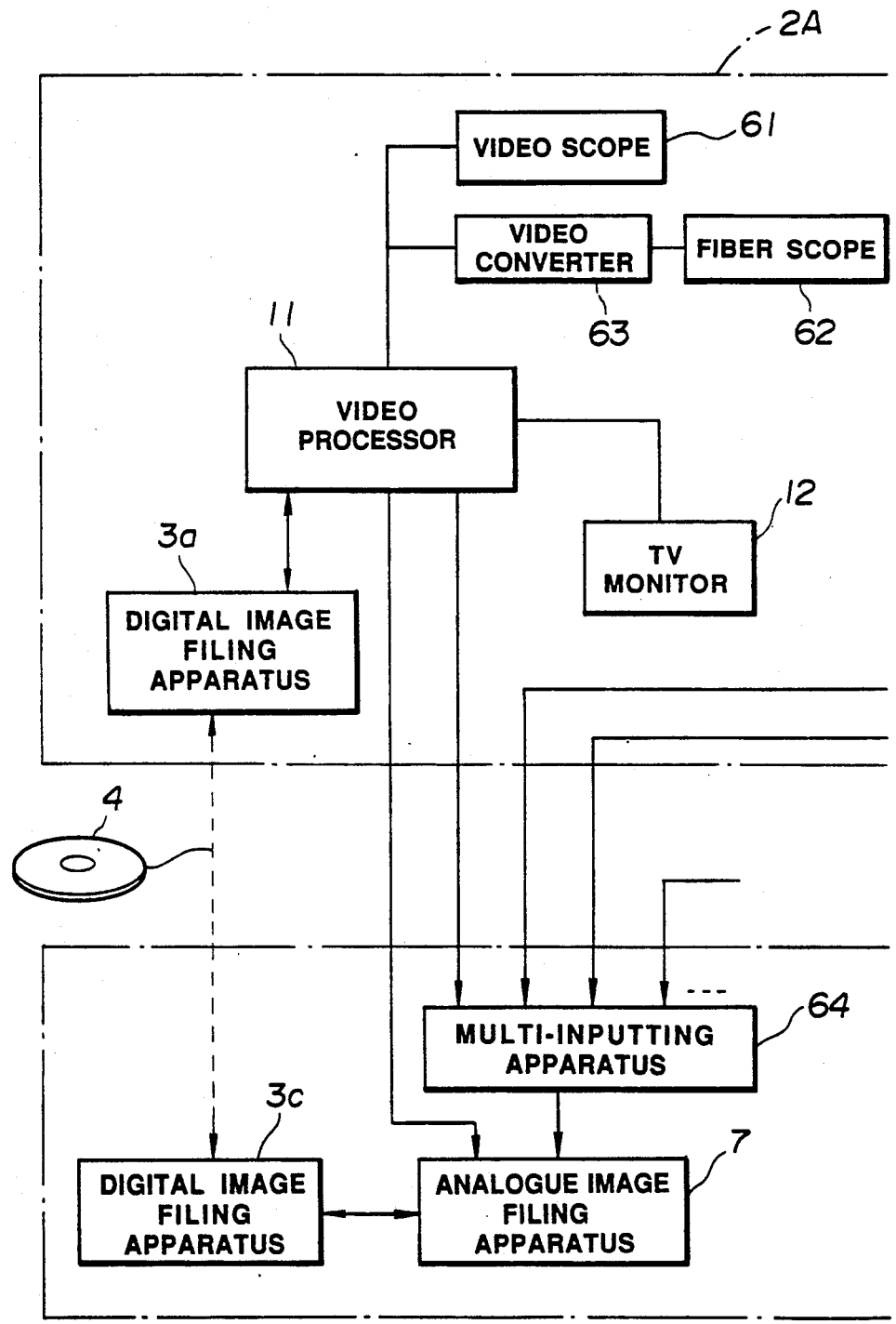

In the digital image filing apparatus 3a of the respective satellite rooms 2I (I=A, B, C), (endoscope) image information and such search information as patient information are recorded in the MO's 4. These MO's 4 are conveyed to the satellite rooms 2I, conference room 2D and concentrated control main room 5 located in various parts of the hospital so that the images may be reproduced (read). As shown in FIGS. 3 and 4, this concentrated control main room 5 has a digital image filing apparatus 3c and analogue image filing apparatus 7.

Figure 2:
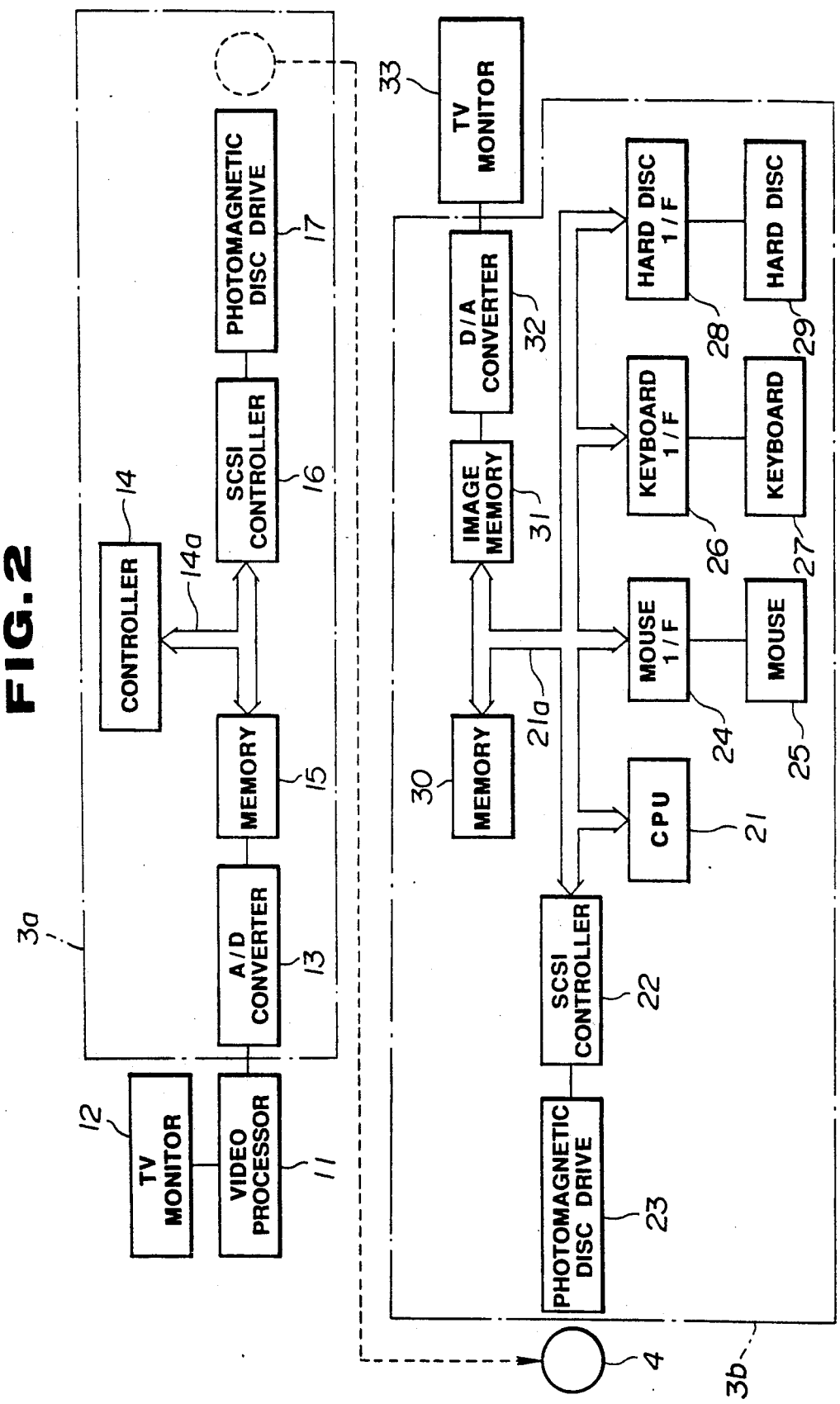

The digital image filing apparatus 3a provided in the respective satellite rooms 2I and the digital image filing apparatus 3b provided in the conference room 2D are formed as in FIG. 2.

An endoscope imaging signal output from such endoscope as an electronic endoscope (video scope) not shown in this drawing is input into a video processor 11 and is converted to a video signal which is input into a TV monitor 12 and the digital image filing apparatus 3a of the satellite rooms 2I. This digital image filing apparatus 3a comprises an A/D converter 13 converting analogue R, G and B video signals of the video processor 11 to endoscope image data which are digital signals, a controller 14 controlling the later described memory 15 and SCSI controller 16, a memory 15 memorizing by the control of the above mentioned controller 14 the above described endoscope image data by the above mentioned A/D converter 13, an SCSI (Small Computer System Interface) delivering to the later described photomagnetic disc drive 17 the endoscope image data memorized in the above mentioned memory 15 by the control of the above mentioned controller 14 and a photomagnetic disc drive 17 recording in the MO 4 which is a recording medium of a comparatively large capacity the endoscope image data of the above mentioned memory 15 input from this SCSI controller 16.

Also, the above mentioned controller 14 applies such various data processes as an image compressing process to the endoscope image data memorized in the above mentioned memory 15 and once memorizes the image data in the above mentioned memory 15 or outputs them to the SCSI controller. In case the above mentioned controller 14 once memorizes in the memory 15 the endoscope image data to which various data processes have been applied as described above, it will output the above mentioned endoscope image data by a predetermined timing from the above mentioned memory 15 to the above mentioned SCSI controller 16.

The above mentioned SCSI controller 16 outputs to the above mentioned photomagnetic disc drive 17 the endoscope image data or the like from the above mentioned memory 15. The above mentioned photomagnetic disc drive 17 records in the MO 4 these endoscope image data or the like. By the way, the video processor 11 is provided with a keyboard not illustrated as a data inputting means to be used in the case of simultaneously recording patient information or the like in recording image information in the MO 4. The keyboard is utilized to input image search data.

The digital image filing apparatus 3b provided in the conference room 2D comprises a microprocessor (called CPU hereinafter) 21 controlling various component devices, a photomagnetic disc drive 23 reproducing the endoscope image data from the above mentioned photomagnetic disc drive 4 and recording various information together with the endoscope image data, an SCSI controller 22 controlling this photomagnetic disc drive 23, a mouse 25 giving an instruction to move a cursor coordinate on the monitor picture to any position, a mouse interface (called a mouse I/F hereinafter) 24 co-ordinating the signal of this mouse 25 and the signal of the above mentioned CPU 21, a keyboard 27 inputting various information to be recorded, for example, into the above mentioned MO 4, a keyboard interface (called a keyboard I/F hereinafter) 26 co-ordinating the signal of this keyboard 27 and the signal of the above mentioned CPU 21, a hard disc 29 in which such various data as image data of a practice program and menu picture are recorded, a hard disc interface (called a hard disc I/F hereinafter) 28 co-ordinating the signal of this hard disc 29 and the signal of the above mentioned CPU 21, a memory 30 used as various process operating regions of the above mentioned CPU 30, an image memory 31 memorizing displaying digital R, G and B video signals and a D/A converter 32 reversely quantizing image data which are digital signals of the above mentioned image memory 31 and converting them to analogue R, G and B video signals so that the analogue R, G and B video signals converted by this D/A converter 32 may be reproduced by a TV monitor 33.

The control signal end and data signal end of the above mentioned CPU 21 are connected through a bus line 21a to the control signal ends and data signal ends of the above mentioned SCSI controller 22, mouse I/F 24, keyboard I/F 26, hard disc I/F 28, memory 30 and image memory 31.

The above mentioned CPU 21 controls by the above mentioned bus line 21a the above mentioned SCSI controller 22, mouse I/F 24, keyboard I/F 26, hard disc I/F 28, memory 30 and image memory 31.

The above mentioned SCSI controller 22 controls the above mentioned photomagnetic disc drive 23, reads out of the MO 4 the above described endoscope image data recorded in the above mentioned satellite room 2I and displays the endoscope image in the TV monitor 33 through the image memory 31 and D/A converter 32.

In case the image is compressed and recorded in the above mentioned MO 4, when it is reproduced, it will be recovered and will be displayed in the monitor picture.

As shown in FIG. 3, the concentrated control main room 5 is provided with a digital image filing apparatus 3c and an analogue image filing apparatus 7 of a large capacity.

The above mentioned digital image filing apparatus 3c comprises a CPU 41 controlling component devices, a memory 42 used as a temporarily storing area or the like of image data or the like, a keyboard 44 connected through a keyboard IF 43 connected to a bus line to input data for searching images or the like, a photomagnetic disc drive 45 capable of reproducing and recording image data recorded in the MO 4, an SCSI controller 46 controlling this disc drive 45 and a communicating means 48 for communication of image data or the like with the analogue image filing apparatus 7, for example, through an optical link cable 47.

On the other hand, the analogue image filing apparatus 7 comprises a CPU 51 controlling component devices, a memory 52 used as a temporarily storing area or the like of image data or the like, a hard disc 54 forming a data base memorizing patient information, inspection information or the like and connected to a bus line through a hard disc I/F 53, an optical disc 56 driven by an optical disc drive 55 and having analogue image information recorded and a communicating means 57 connected with the bus line, connected with the communicating means 48 of the digital image filing apparatus 3c through the above mentioned optical link cable 47 and making communication of search information or the like.

As both image filing apparatus 3c and 7 are connected with each other by the above mentioned optical link cable 47, in case a serial number is registered in the MO 4 full, for example, of image data or the like, the search information and serial number will be transmitted also to the analogue image filing apparatus 7 through this optical link cable 48, will be registered in a hard disc 54 which is a data base of the analogue image filing apparatus 7 and will be able to be controlled en bloc or concentrated and controlled.

The formations of the apparatus within such respective rooms as the respective satellite rooms 2I and conference room shall be explained in the following by using FIGS. 4 to 8.

As shown in FIG. 4, each video processor 11 within the endoscope inspection satellite room 2A is used as connected with an externally fitted scope having a video converter (TV camera) 63 fitted to a video scope 61 or fiber scope 62 having an imaging means built-in. This video processor 11 can process a signal and can display an endoscope image in a TV monitor 12 or can record a digital endoscope image in the MO 4 set in the digital image filing apparatus 3a connected to the above mentioned video processor 11. It can also read out endoscope image data recorded in any MO 4 set in the digital image filing apparatus 3a connected to this vedeo processor 11 and can reproduce them in the TV monitor 12.

Further, each video processor 11 is connected with the analogue image filing apparatus 7 of a large capacity through a multi-inputting apparatus 64 within the concentrated control main room 5 through an analogue video signal line so that the analogue video signal output from the video processor 11 may be recorded in this analogue image filing apparatus 7. Also, each video processor 11 is connected with the analogue image filing apparatus 7 through a communication line so that image information or the like relating, for example, to an analogue image may be transmitted. By the way, the endoscope inspection satellite room 2A shown in FIG. 4 is provided with, for example, three digital image filing apparatus 3a as shown in FIG. 1 and the video processor 11 or the like shown in FIG. 4 is connected to each image filing apparatus 3a so that an analogue image may be recorded in the analogue image filing apparatus 7 through the multi-inputting apparatus 64 from each video processor 11. This analogue image is recorded in the optical disc 56 fitted to the optical disc drive 55 shown in FIG. 3 and its search information, that is, the patient information and inspection information and the track number of the analogue image recorded in the optical disc 56 are registerd in the hard disc 54 and are made a data base.

By the way, in case the MO 4 fitted to the digital image filing apparatus 3a becomes full of image data or the like, when this MO 4 is moved to be set in the digital image filing apparatus 3c within the concentrated control main room 5 as shown by the broken line in FIG. 4, a serial number will be able to be imparted to the MO 4 and will be thereby registered in the data base of the analogue image filing apparatus 7.

By the way, whether the image information from the video processor 11 is recorded as a digital image in the digital image filing apparatus 3a or as an analogue image in the analogue image filing apparatus 7 can be freely selected with a switch provided on the operating panel or the like so that it may be recorded in only one or in both.

As shown in FIG. 5, the X-ray satellite room 2B is provided with a set of the video scope 61, video processor 11, TV monitor 12 and digital image filing apparatus 3a in the endoscope inspection satellite room 2A shown in FIG. 4.

The video processor 11 is connected with the digital image filing apparatus 3a through an RGB signal line and data line and can compress and record endoscope images. This digital image filing apparatus 3a can make an image recording operation with a foot switch. The video processor is connected also with the TV monitor 67 so that the compressed and recorded image may be recovered and may be reproduced in the TV monitor 67.

In case the MO 4 set in this digital image filing apparatus 3a becomes full of records in the memorizing capacity, the MO 4 will be conveyed also to the concentrated control main room 5, will be given a serial number and will be controlled en bloc in the analogue image filling apparatus 7.

By the way, the same as in the case of FIG. 4, the video processor 11 can also transmit an analogue video signal to the multi-inputting apparatus 64 within the concentrated control main room 5 through the analogue video signal line.

The operation satellite room 2C shown in FIG. 6 comprises, for example, an abdominal cavity scope set 68, externally fitted television camera apparatus 69 (formed, for example, of a video converter, video processor and TV monitor), digital image filing apparatus 3a connected with this externally fitted televisiion camera apparatus 69 through an RGB signal line and data line and recording with digital images, TV monitor 67 and foot switch 66. Also, in this digital image filing apparatus 3a, the MO 4 having become full is conveyed to the concentrated control main room 5, is given a serial number and is controlled en bloc by the analogue image filinng apparatus 7 of the concentrated control main room 5.

In the conference room 2D shown in FIG. 7, the digital image filing apparatus 3b and TV monitor 33 shown in FIG. 2 are arranged and, when the MO 4 recorded in the digital image filing apparatus 3a of the other satellite room 2I is conveyed and is fitted to this digital image filing apparatus 3b, the image will be able to be reproduced.

The concentrated control main room 5 used to register the serial number of the MO 4 recorded in the above mentioned respective satellite rooms 2I or to search images is provided with not only the digital image filing apparatus 3c and analogue image filing apparatus 7 shown in FIG. 3 but also an automatic photographing apparatus 71 and film image inputting apparats 72 shown in FIG. 8.

In FIG. 8, RGB signals are input into the multi-inputting apparatus 64 within this concentrated control main room through wired RGB signal lines from the video processors 11 of the respective satellite rooms 2I. In this multi-inputting apparatus, by switching the video lines, the images of a plurality of video processors 11 can be recorded in one analogue image filing apparatus 7.

This analogue image filing apparatus 7 outputs a video signal to the automatic photographing apparatus 71 so that the image displayed on the monitor picture may be photographed with a 16 mm camera or 35 mm camera and may be made a film.. The digital image filing apparatus 3c also outputs a video signal to this automatic photographing apparatus 71 and can also make the image a film.

Also, the film image inputing apparatus 72 can output an NTSC and RGB signals respectively to the analogue image filing apparatus 7 and digital image filing apparatus 3c. This film image inputting apparatus 72 makes a video signal by scanning a film with an image reading apparatus and outputs the video signal to the analogue image filing apparatus 7 or digital image filing apparatus 3c so that the film image may be made a video image, may be recorded as an analogue image or digital image and may be controlled en bloc.

By the way, the analogue image filing apparatus 7 transmits the recorded analogue image to the digital image filing apparatus 3c and can record it as a digital image and the digital image of the digital image filing apparatus 3c is also transmitted to the analogue image filing apparatus 7 and can be recorded as an analogue image.

In the case of recording endoscope images in the respective satellite rooms 2I as described above, they can be freely recorded as digital images or as analogue images by a switch or the like on the front panel.

The approximate standard of this selection is as shown in FIG. 9. (By the way, in FIG. 9, the video scope system 75 is shown to be of the video scope 61, video processor 11 and TV monitor 12, for example, in FIG. 4.)

There are features that the analogue image filing apparatus 7 is of such large capacity that, for example, about 100,000 sheets of an endoscope image can be recorded with an analogue picture quality of a middle degree and the image can be reproduced substantially at a moment.

On the other hand, the number of endoscope image sheets which can be recorded by compression in the MO 4 of the digital image filing apparatus 3a or the like is about 5000 sheets. As it is a digital image, the picture quality is higher than of an analogue image. There is an advantage that, even if the reproduction is repeated, the picture quality will not deteriorate. By the way, the reproduction takes a time longer than by the analogue image filing apparatus 7.

Therefore, the analogue image filing apparatus 7 is often used for recorded images for such uses as of routine images and normal images.

On the other hand, the digital image filing apparatus 3c is often used for recorded images for such uses as of images to be published by societies, image processing images, images viewed precious and images wanted to be seen in another place.

Now, in the digital image filing apparatus 3a set in each satellite room 2I, as shown in FIG. 10, the patient information,. inspection information and chart information together with the image information (shown, for example, by the images 1 to 20) photographed during the inspection are recorded in the MO 4.

The patient information consists of patient ID, patient name, date of birth and sex data. The inspection information consists of inspection date and.. inspection time data, Chart data made for each inspection are recorded as chart information. The patient information can be used as a patient identification. The inspection date or the like can be used as an inspection identification. Therefore, in each MO 4, there are such data bases as image information, patient information for controlling or searching such image information and inspection information.

In case the above mentioned MO 4 becomes full of image information and the like, the MO 4 will be conveyed to the concentrated control main room 5 and will be set in the digital image filing apparatus 3c in this room, a serial number will be imparted to the MO 4, a registering operation to a large capacity data base controlling the entire MO 4 will made as in FIG. 11 and, as a result, such data base as an example shown in FIG. 12 will be made.

Figure 11:
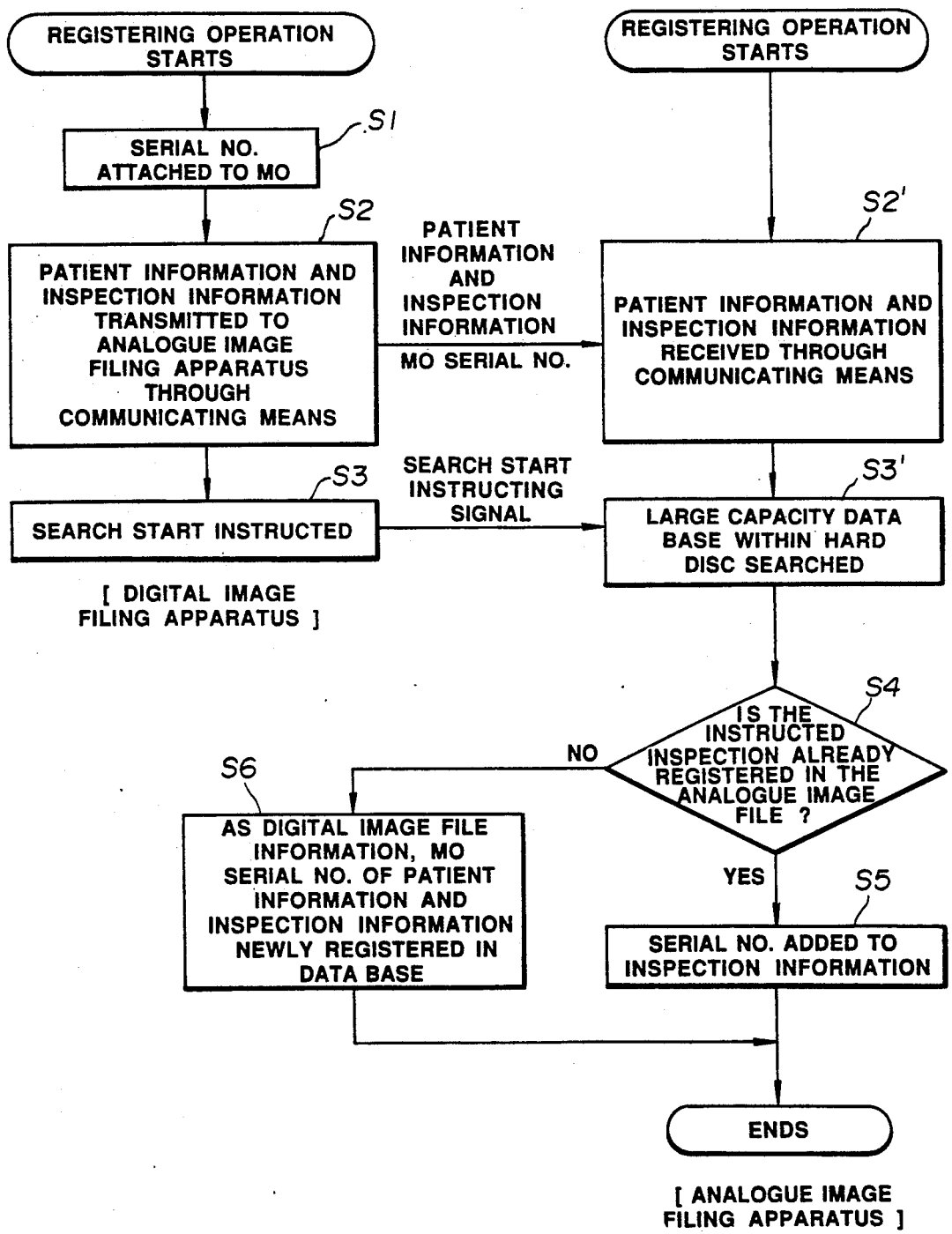

As shown in FIG. 11, when the MO 4 having become full is set in the digital image filing apparatus 3c and the registering operation starts, in step S1, a serial number (for example, P) will be imparted to the MO 4 and then the process will move to step S2. In this step S2, the patient information and inspection information within the MO 4 are read out and the patient information, inspection information and serial number of the MO 4 are transmitted to the communicating means 57 on the analogue image filing apparatus 7 side from the communicating means 48 through the optical link cable 47 shown in FIG. 3. The receiving means on the analogue image filing apparatus 7 side receives in step S2' the transmitted patient information and inspection information, then receives the delivery (step S3) of a search start instructing signal instructing a search start from the digital image filing apparatus 3c side, searches the large capacity data base within the hard disc and carries out the step S3' of searching whether the inspection of the above mentioned patient information and innspection information is present or not. Then the process moves to the next step S3'.

In this step S4, it is judged whether the designated inspection is already registered in the analogue image filing apparatus 7 or not.

As a result of the inspection, in case the designated inspection is already present in the analogue image filing apparatus 7 (that is, in the case of the inspection recorded in the digital image filing apparatus 3a in the satellite room 2I and recorded also in the analogue image filing apparatus 7), the step S5 of additionally registering the serial number of the MO 4 in the inspection information already existing in the large capacity data base will be made.

The process results of this step S5 are as in FIG. 12.

As shown in FIG. 12(a), a serial number, for example, P is imparted (process of step S1) to the MO 4 on the digital image filing apparatus 3c side. The respective patient information and inspection information have been simultaneously recorded in the digital image information in an inspection of this MO 4.

As shown in FIG. 12(b), the (analogue) images of the same patient informatiion and inspection information exist and the track number of the optical disc 56 in which these images are recorded has been simultaneously recorded. In this case, as shown in FIG. 12(b), the serial number P of the MO 4 will be further additionally registered in the data base of the patient information and inspection information of this inspection and the track number of the optical disc.

On the other hand, returning to FIG. 11, in case the images of the designated patient information and inspection information have not been recorded in the analogue image filing apparatus 7, the judgment of the step S4 will be NO and the process of step S6 will be made. In this step S6, the patient information and inspection information shown in FIG. 12(a) and the serial number (P in this case) are processed to be registered in the data base and this registering operation ends (in fact, when the process of the step S2 to S6 is repeated and the process ends for all the inspections recorded in the MO 4, this registering operation will also end).

Thus, in the data base within the analogue image filing apparatus 7, not only the analogue image is made a data base and is contnrolled but also the digital image is made a data base and the analogue/digital images are integrally controlled (en bloc).

It is one of the features of this first embodiment that either of the analogue image and digital image can be searched by the large capacity data base within the concentrated control main room 5.

Therefore, when the patient information (for example, the patient ID) and inspection information (for example, the inspection date) to be searched are input from the keyboard 44, for example, of the digital image filing apparatus 3c within the concentrated control room 5, the digital image filing apparatus 3c will search the large capacity data base within the analogue image filing apparatuks 7 and will display in a display in what serial number of the MO 4 the designated inspection exists.

This manner is shown in FIG. 13.

For example, when the patient ID (represented, for example, by 100) and inspection date are input, if they have been recorded in both of the analogue image and digital image, A and D representing that either image is present will be displayed and it will be displayed that this digital image is recorded in the MO 4 of a serial number, for example, of 50.

Also, if they have been recorded in only the analogue image, only A will be displayed and, if they have been recorded in only the digital image, the serial No. 50 of the MO 4 in which this digital image has been recorded will be displayed together with D.

Therefore, in what serial number of the MO 4 they are recorded is found and, when the operator pulls the MO 4 of that serial number out of such MO 4 storing place as a shelf, conveys it to the digital image filing apparatus 3b, for example, within the conference room 2D, sets it in the digital image filing apparatus 3b and inputs the patient ID and inspection date from the keyboard 27, the designated searched image will be searched out of the small capacity data base present in the MO 4 and will be displayed in the monitor 33. Also, the MO 4 may be set in the digital image filing apparatus within another satellite room 2I so as to display any desired searched image.

By the way, it is needless to say that any desired analogue image can be searched in the concentrated control main room 5.

According to this first embodiment, a serial number to be medium discriminating information is imparted to each (recorded) MO 4 full of recorded images,. the search information of the image information recorded in the MO 4 is registered in the large capacity data base together with the serial number and the respective recorded MO's 4 are all controlled en bloc in the large capacity data base. Therefore, in the concentrated control main room, if such search information as the patient ID is input to search a desired image, the serial number of the recorded MO 4 in which the image corresponding to the search information will be displayed. Therefore, if the searcher sets the MO 4 of that serial number in the nearest digital image filing apparatus 3$i$ (i=a, b, c) and inputs the above mentioned search information, the desired image will be able to be searched and displayed.

Also, according to this first embodiment, as the digital image and analogue image are controlled en bloc in the large capacity data base, either image can be searched in one place. (The respective data bases of the digital image and analogue image need not be respectively searched.)

Also, in this first embodiment, the MO 4 can be conveyed to reproduce or search images in the digital image filing apparatus 3$i$ in each place in the system 1 and therefore a system which can control respective MO's 4 en bloc and is easy to use can be realized at a low cost.

Further, even in case the satellite rooms and conference rooms are increased by providing hospital buildings, if the above described system component devices are set in such rooms, a system which can make a control en bloc will be able to be maintained without changing others and the expansion will be able to be easily coped with.

Figure 15:
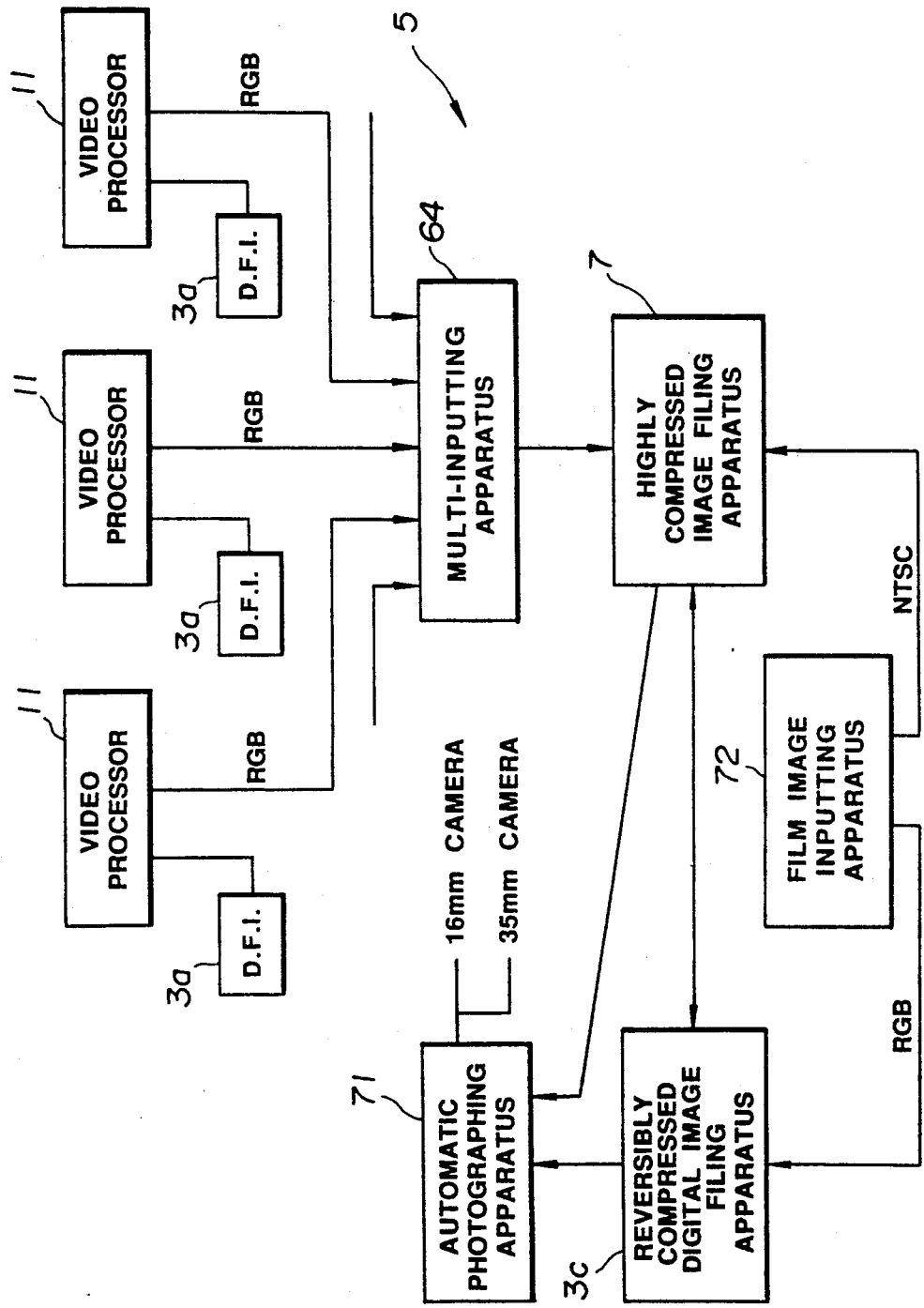

In the modification shown in FIGS. 14 and 15, a high compression digital image filing apparatus is used instead of the analogue image filing apparatus of the above described first embodiment.

Generally, in the case of the digital recording, the image will be compressed in recording. In such compression, generally, if the compression rate is elevated (the compression is made higher), the image data to be recorded will decrease and a large amount of image data will be able to be recorded but, on the other hand, the picture quality will deteriorate. On the contrary, if the compression rate is depressed, for example, in the case of a reversible compression, the compression rate will not be high but, at the time of the recovery, the image will always return to the original image and therefore the picture quality will not reduce but will be high.

Therefore, in this modification, as shown in FIG. 15, the routine image is recorded in a high compression image filing apparatus 7 but the important image is recorded in a reversible compression digital image filing apparatus.

Figure 16:
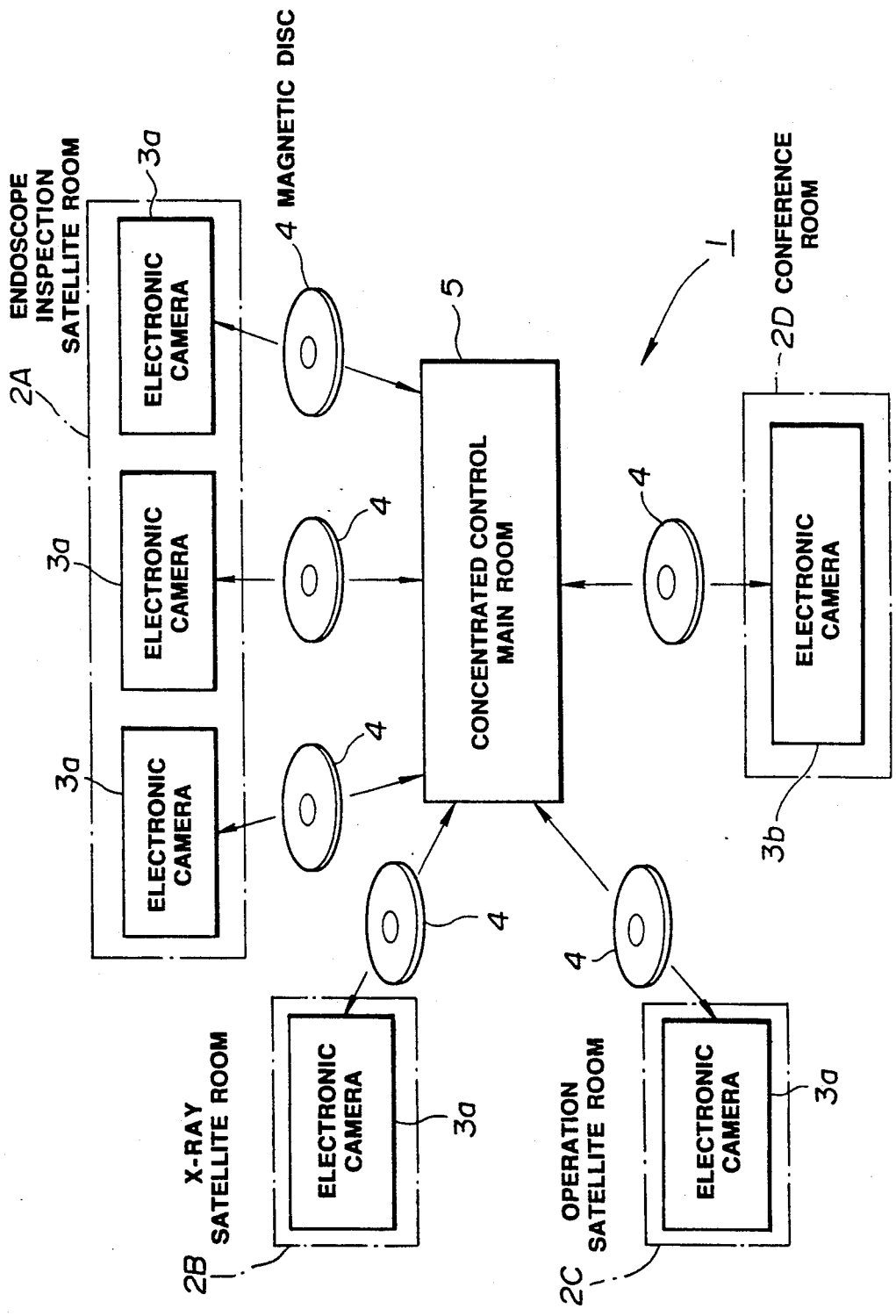
FIGS. 16 and 17 relate to the second embodiment of the present invention.
Figure 17:
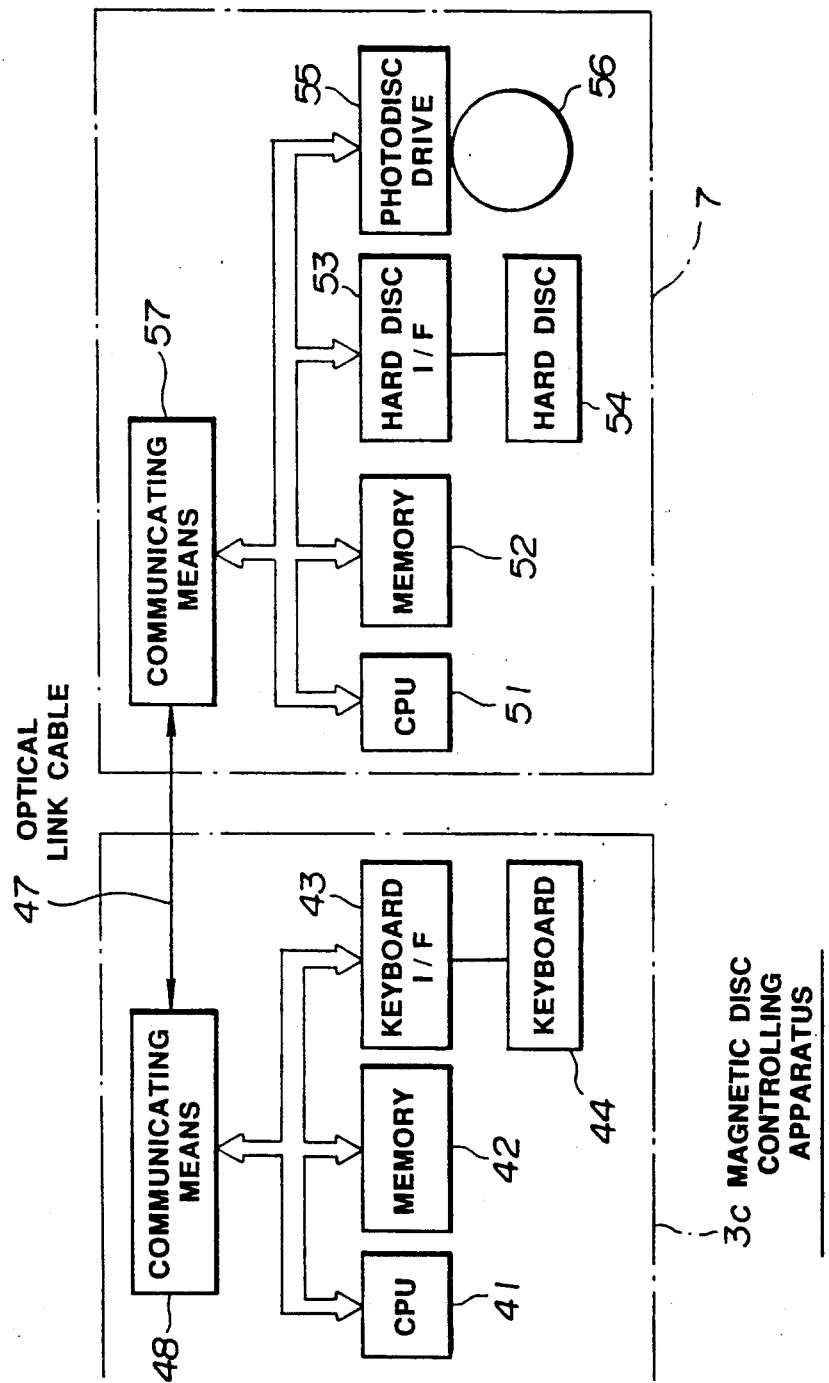

In the second embodiment shown in FIGS. 16 and 17, an electronic camera apparatus for recording a photoelectrically converted object image in a flexible magnetic disc (for example, of 2 inches) is used instead of the digital image filine apparatus used in the first embodiment. In this embodiment, the photomagnetic disc of the first embodiment is replaced with a flexible magnetic disc (of 2 inches) and 50 sheets of an analogue image can be recorded in this magnetic disc. Therefore, in this embodiment, one inspection amount (about 40 sheets) can be recorded in one magnetic disc. By the way, such search information as the patient ID number is not recorded in this magnetic disc.

As shown in FIG. 17, when the magnetic disc of the concentrated control main room 5 is to be registered, the operator will input from the keyboard such search information as the patient ID number in the image recorded in the magnetic disc and the disc number of the magnetic disc.

By the way, in this invention, the above described first embodiment, modification and second embodiment may be combined to be worked.

Figure 18:
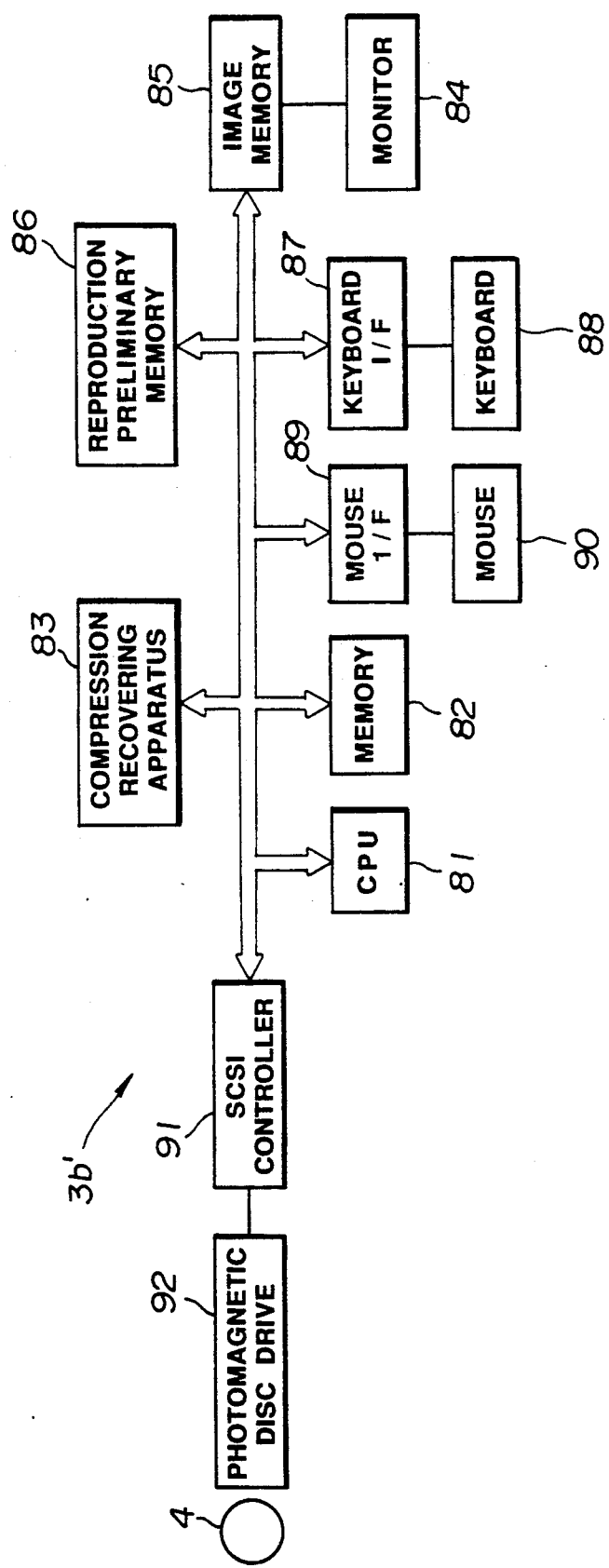

FIG. 18 shows the formation of a digital image filing apparatus 3$b'$ provided in the conference room 2D in the third embodiment of the present invention.

This digital image filing apparatus 3$b'$ comprises a CPU 81 controlling the component devices of this apparatus 3$b'$, a memory 82 to be a work area by this CPU 81, a compressing and recovering apparatus 83 for compressing image data and recovering the compressed image data, an image memory 85 in which image data displayed in a monitor 84 are stored, a reproduction preliminary memory 86, a keyboard 88 connected through a keyboard I/F 87 to input such data as patient information and search information, a mouse 90 connected through a mouse I/F 89 to select and designate a contracted image displayed in the monitor 84 and a photomagnetic drive 92 connected through an SCSI controller 91.

An original image read out of the photomagnetic disc drive 92 and recovered by the compressing and recovering apparatus 83 is stored in the above mentioned reproduction preliminary memory 86. This reproduction preliminary memory 86 is of a capacity which can store four sheets of an image. For example, four sheets of an image stored in this reproduction preliminary memory 86 can be displayed at once in the monitor 84 as shown in FIG. 20($b$) through the image memory 85 Also, the image registered in this reproduction preliminary memory 86 can be deleted by an image unit and another image can be registered again in the vacant space.

Figure 20:
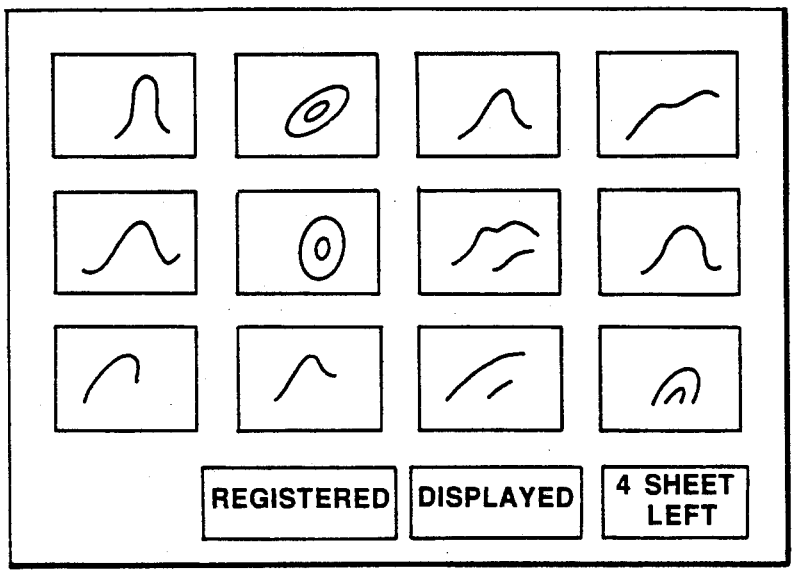
Figure 20:
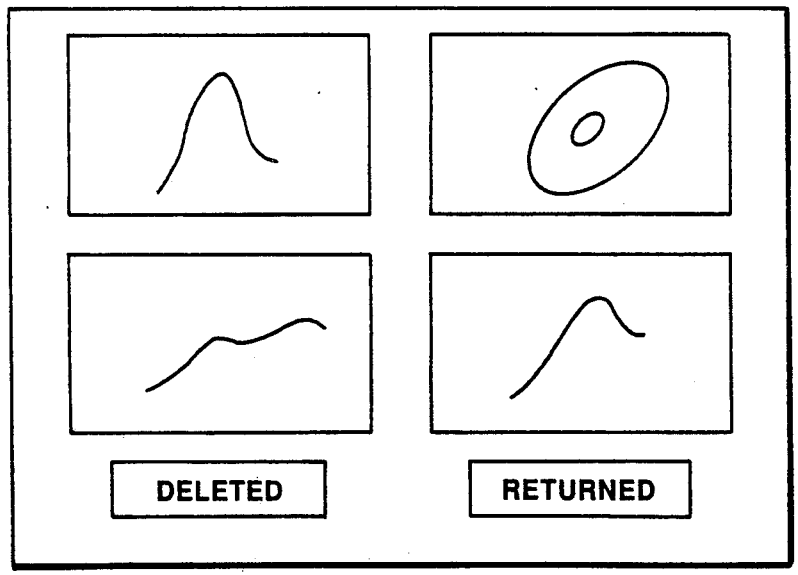

In this embodiment, in case search information is input, the image corresponding to the search information will be contracted to be a contracted image as shown in FIG. 20($a$) and, for example, 12 sheets of the contracted image will be able to be displayed at once. In case any desired search image in these contracted images is selected, compared and searched (displayed), if a plurality of contracted images are selected, for example, up to four sheets of the original image of the selected contracted image will be able to be displayed at once as shown in FIG. 20($b$).

The process contents relating to the display of any desired search image in this second embodiment are as in FIG. 15.

When the process mode of a comparing search starts, first of all, in step S1, such search information as the patient ID and inspection date will be input from the keyboard 88 and the corresponding inspection will be selected.

By this step S1, the CPU 81 controls the image corresponding to the designated inspection so as to be read out of the MO 4, transfers the contracted image data of the image data to the image memory 85 and displays the contracted images as shown in FIG. 20($a$).

When the operator selects by the mouse 90 a contracted image of the image desired to be compared in these contracted images, the step S2 of storing in the reproduction preliminary memory 86 the comparison object image data of the contracted image selected under the control of the CPU 81 will be made by receiving this selection. That is to say, the compressed image data read out of the MO 4 are recovered by the compressing and recovering apparatus 83 and are stored in the reproduction preliminary memory 86. After this step S2, in case the other contracted images are desired to be displayed as comparison object images, in the next step S3, if YES is selected in the judgment of whether the other images are to be registered or not, the process will again return to the step S1 and therefore the other images will be able to be also stored in the reproduction preliminary memory 86. In case the process returns to the step S1, an image of another inspection will be able to be selected and not only optical endoscope images but also ultrasonic images by ultrasonic endoscopes or X-ray images may be selected.

At most four sheets of an image wanted to be compared can be stored in the reproduction preliminary memory 86.

In the step S3, in case the other images are not desired to be registered, if NO is selected, at most four sheets of the original image data stored in the reproduction preliminary memory 86 will be simultaneously displayed as shown in FIG. 20(b).

When this function is used, the variation with the lapse of time of the affected part of the same patient and the image, for example, by a video scope, ultrasonic endoscope image and X-ray perspective image displayed and an auxiliary means very effective to the general diagnosis will be able to be provided.

The third embodiment shall be explained in the following.

In this embodiment, for example, the front surface recording region and back surface recording region of a photomagnetic disc are combined to be controlled as one recording region, that is, as one recording mediium.

In each of the above described embodiments, the front surface recording region and back surface recording region (in case recording can be made also on the back surface) of a photomagnetic disc are controlled by attaching separate serial numbers to them, because the generally used photomagnetic disc driving apparatus (reference numerals 17 and 23 in FIG. 2) is provided with only one writing-in/reading-out head and therefore the front surface and back surface can not be simultaneously accessed. Therefore, in FIGS. 11 and 12, in case, for example, the nth used Mo is to be registered, a serial number of "2" will be alotted to its front surface recording region and a serial number of "2+1" will be alotted to its back surface recording region. Thereby, the front surface recording region and back surface recording region of the Mo will be controlled as entirely separate recording media.

On the other hand, in this third embodiment, there is used a photmagnetic disc driving apparatus of a 2-head type wherein both front and back surfaces can be simultaneously accessed.

In this embodiment, as both surfaces can be simultaneously read out, it is not necessary to control the front and back surfaces by attaching respective serial numbers to them as in the above described embodiment. Therefore, in this third embodiment, in FIGS. 11 and 12, in case an Mo intended to make, for example, the nth registration is to be registered, a serial number of "n" will be alotted to the Mo and the informations recorded on the front and back surfaces will be able to be combined to be controlled with one serial number of "n".

The fourth embodiment shall be explained in the following.

In this embodiment, a keyboard for inputting the patient informations from the digital image filing apparatus side is added to the first embodiment.

In the above mentioned first embodiment, as shown in FIG. 2, the patient informations (ID No., name,. etc) to be recorded together with the image information in the Mo 4 are input from the keyboard provided on the video processor side. However, in this fourth embodiment, a keyboard is provided in the image filing apparatus 3a set in the satellite room or the image filing apparatus 3c provided in the concentrated control room in FIG. 2 to input patient data into the Mo from the image filing apparatus side.

Figure 21:
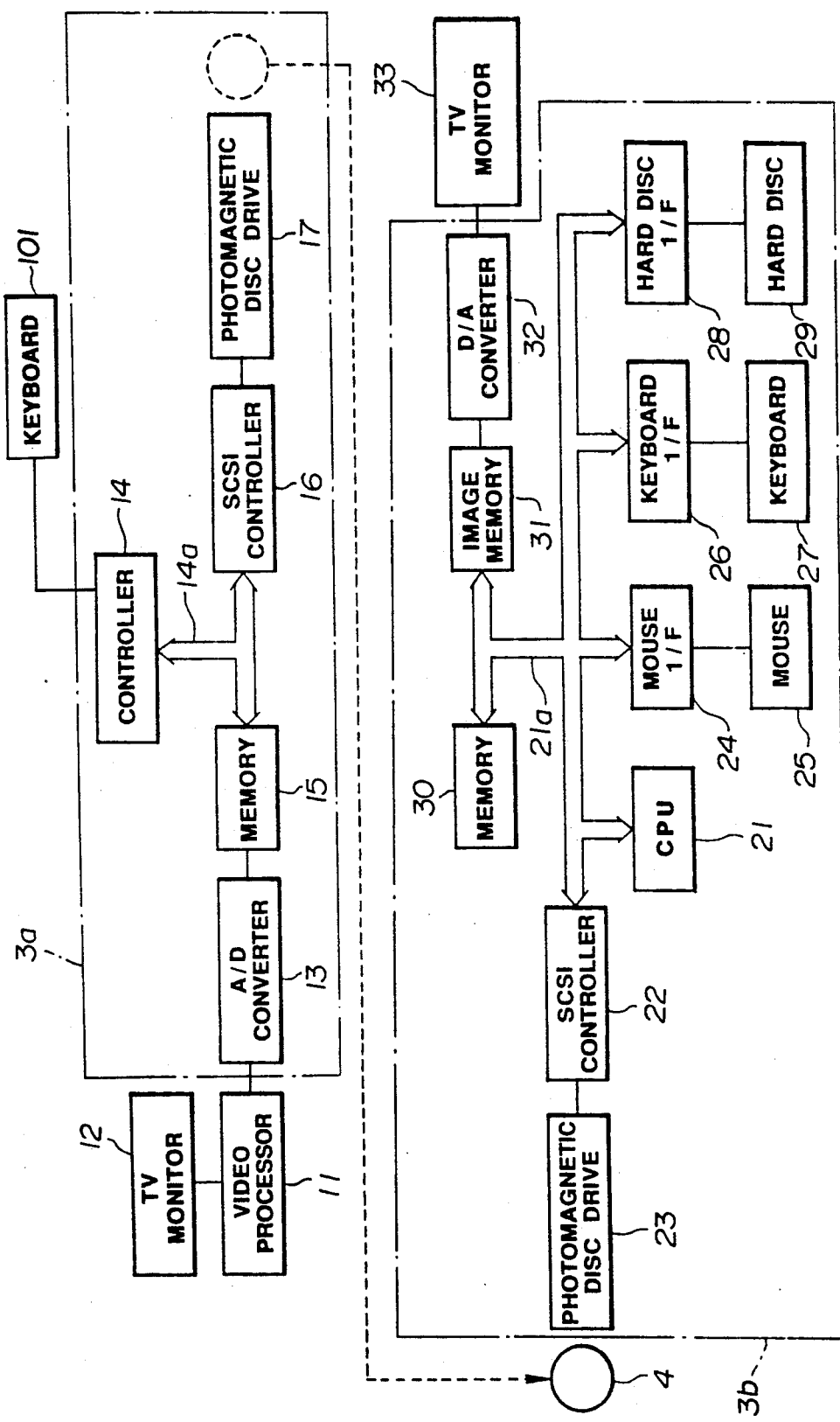
FIG. 21 is a formation diagram of a digital image filing apparatus showing the fourth embodiment.

As shown in the attached FIG. 21, the image filing apparatus 3a is provided with a keyboard. Patient data input from this keyboard 101 are written as image data into Mo through a controller 14, SCSI controller 16 and photomagnetic disc driving apparatus 17.

Also, the digital image filing apparatus 3c for the concentrated control room shown in FIG. 3 is provided with a keyboard for inputting search data. This keyboard can be used also as a keyboard for inputting and correcting/adding patient data. For example, in the image filing apparatus 3a of the satellite room, only an ID No. is input and, in the case of registering the Mo, such additional patient data as a name and age may be additionally noted.

Thereby, at the time of the inspection, in the satellite room, only the ID No. may be input and the other patient data can be later input en bloc. Thus, the efficiency of the inspection will rise.

The fifth embodiment shall be explained in the following.

In this embodiment, the compression rate is altered later. In the above described first embodiment, images are compressed by the image filing apparatus 3a set in the satellite room and are recorded in the Mo. On the other hand, in the fifth embodiment, in the image filing apparatus 3a set in the satellite room, the compression rate can be variably selected in response to the importance of the image and, in the image filing apparatus 3b set in the conference room, the compression rate selected anyhow in the image filing apparatus 3a at the time of the inspection can be altered after the image is confirmed at the time of the conference.

Figure 22:
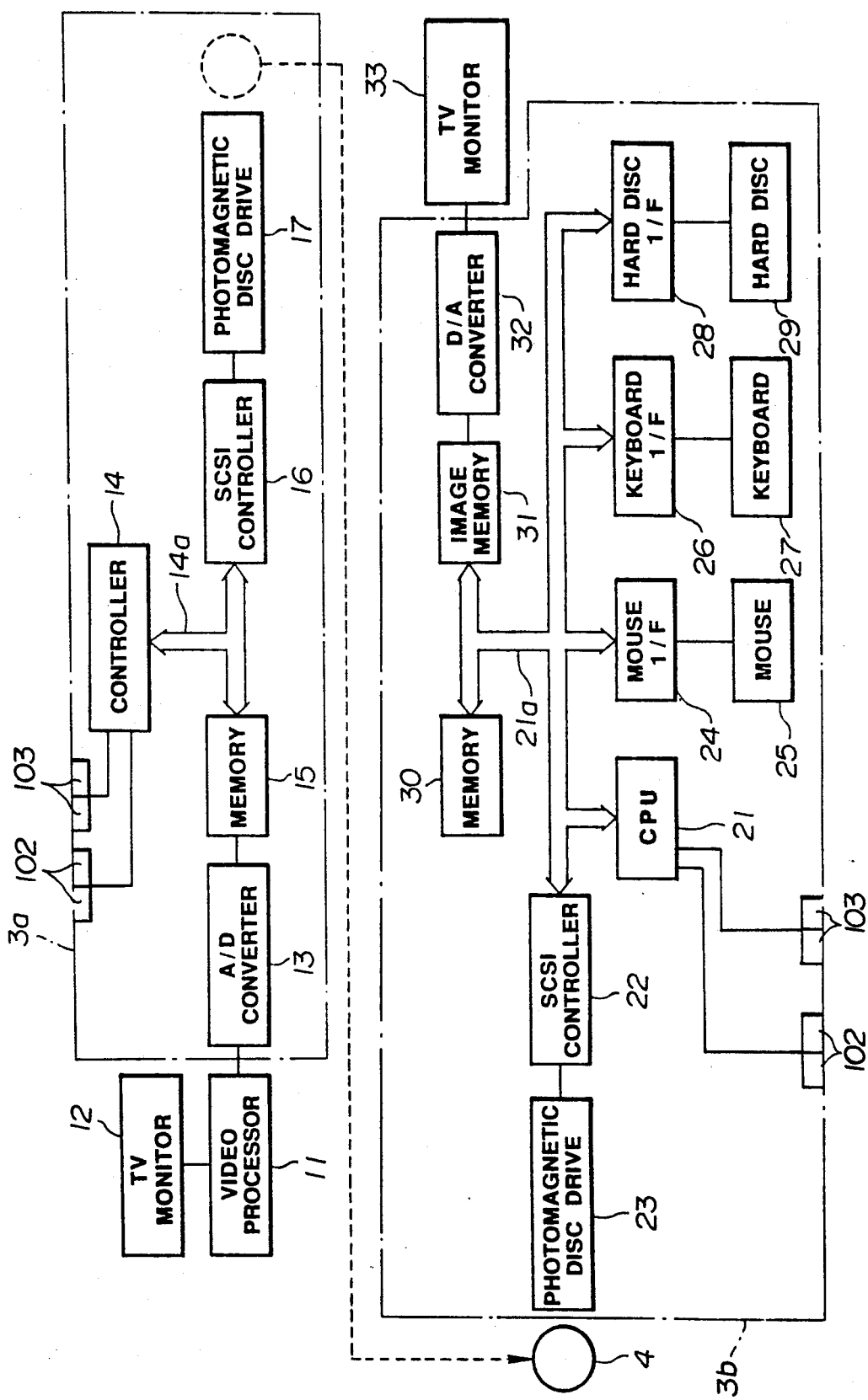
FIG. 22 is a formation diagram of a digital image filing apparatus showing the fifth embodiment.
Figure 23:
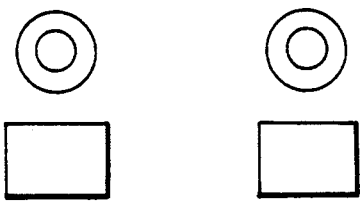
FIG. 23 is an explanatory view showing a part of a front panel of a digital image filine apparatus.

In this embodiment, as shown in FIGS. 22 and 23, compression rate selecting switches 102 and compression rate displaying LED's 103 are provided on the front panel of the image filing apparatus 3a set in the satellite room.

Here is the following relation between the compression rate and picture quality:

½-compression rate mode—The compression is called a "reversible compression". At time of the compression/restoration, it will be made without losing the image information at all. Therefore, the picture quality is the best. (The restored image is exactly the same as the original image before the compression.) However, the compression rate is ½ and is not so high. Therefore, the number of sheets which can be recorded in the Mo is small.

1/10-compression rate mode—The compression is called a "irreversible compression". At the time of the compression/restoration, the image information will be cut to such degree as has no influence on the diagnosis. Therefore, the picture quality after the restoration is of an ordinary degree. The compression rate is 1/10 and is high. Therefore, the number of shets which can be recorded in the Mo is large.

At the time of the inspection, the user will select the compression rate by the following criteria. That is to say, when the above mentioned compression rate selecting switch 102 is pushed to select the compression rate, the LED 103 will be selected in response to it and will be lighted to display the compression rate:

(a) Important disease example for which the image is wanted to be processed later:

Precious disease example wanted to be published in the society or the like later:

Compression rate of ⅓ is selected.

(b) Routine disease example (general disease example) Compression rate of 1/10 is selected.

(c) Disease example which can not be judged to be either of (a) and (b) above:

Compression rate of ⅓ is anyhow selected.

Then, the image for which the compression rate has been selected as mentioned abve and which has been recorded in the inspection room can be read out, displayed and read in the filing apparatus 3b having the Mo 4 set in the conference room.

Figure 24:
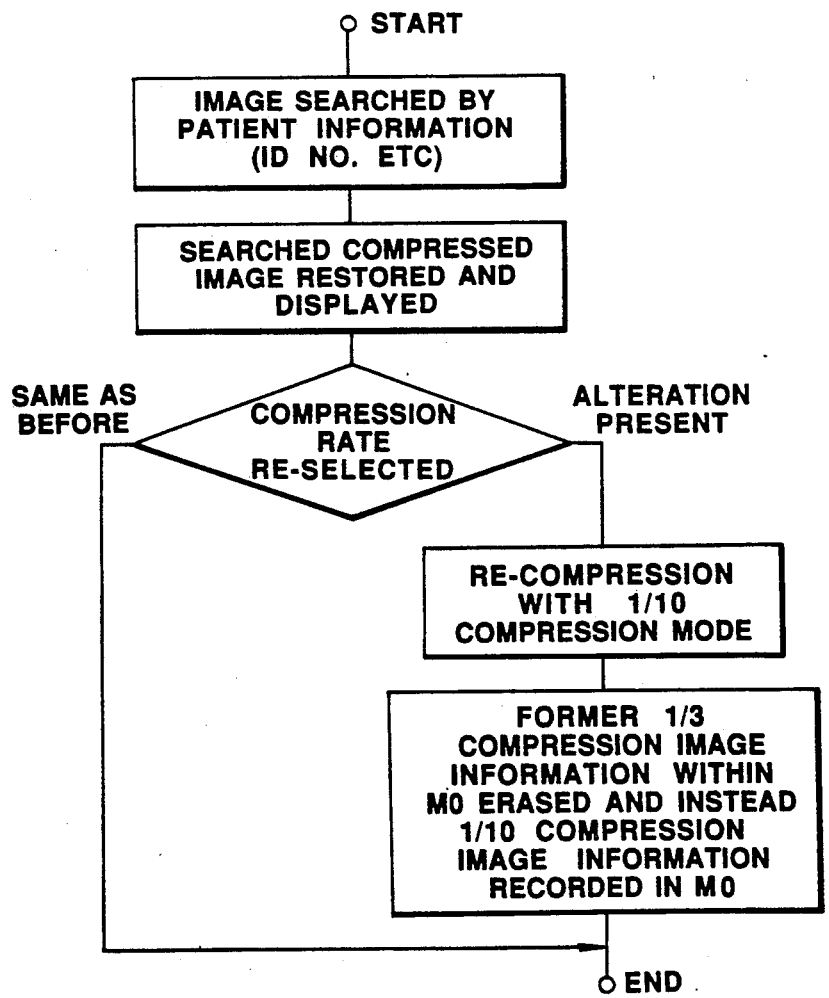
FIG. 24 is a flow chart showing a flow of the fifth embodiment.

In such case, the image reader can confirm the restored and displayed image and can re-select the compression rate again (however, the alteration from ⅓ compression to 1/10 compression is possible but naturally the alteration of 1/10 compression to ⅓ compression is impossible). That is to say, such SW 102 and LED 103 as in FIG. 22 are provided also on the front panel of the filing apparatus 3b set in the conference room. By using this switch 102, for example, the image selected by the criterion in (a) above is re-confirmed, then the image not judged to be so important and the image recorded at a compression rate of ⅓ anyhow by the above mentioned criterion (C) are re-confirmed. When the image reader pushes the 1/10-compression selecting switch 102 for the image judged to be sufficient [corresponding to the above mentioned criterion (6)] to be handled as a routine image. the image will be re-compressed by the 1/10-compression mode and will be re-recorded in the Mo (in such case, the previous ⅓-compression image information will be erased). The above mentioned procedure is shown in the flow chart in FIG. 24.

In this embodiment, at the time of the inspection, the image is recorded anyhow by the high picture quality compression mode and later the compression rate can be selected again while observing the image in detail. Therefore, the efficiency in the inspection will rise and the number of recorded sheets will increase.

By the way, in case a digital image is to be recorded in the MO 4 in the satellite room 2I, for example, in the first embodiment, the image may be recorded with or without compression. (By the way, in case the image is compressed, a recovering function will be also provided.)

Also, for example, in the first embodiment, the medium discriminating information of the respective MO's 4 is imparted to the MO 4 having become full of images and the search information and medium discriminating information are registered in the large capacity data base. However, the information of the MO 4 before becoming full of images may be also registered in the large capacity data base. In this case, for example, the registration date and time and the like will be recorded on the data base side or the like and then, in case the MO 4 becomes full of images and the search information (relating to the image recorded after the registration) is to be registered, only the search information required to be registered may be made easy to register. Also, as the image information or the like may be rewritten in some case, the discriminating information as to whether the MO 4 has been recorded or not may be registered simultaneously with registering it in the data base.

The recorded MO's 4 may be re-edited so that the image information relating, for example, to the same patients may be recorded en bloc in the same MO 4 as much as possible. (The newly edited MO 4 may be reproduced so that the search or the like may be easy.) In case the endoscope inspection and ultrasonic inspection are simultaneously used, for example, on the same patient, generally they will be recorded in separate MO's 4 and therefore will be easy to use in the case of the general diagnosis.

In the case of making a data base, if the data base amount becomes large, the search will take time and therefore may be made easy as by re-editing.

It is apparent that, in this invention, working modes different in a wide range can be formed on the basis of this invention without deviating from the spirit and scope of the invention. This invention is not restricted by its specific working modes except being limited by the appended claims.

What is claimed is:

1. An endoscope image filing apparatus characterized by comprising:

a recording means for recording in the same medium endoscope image information and search information required to search the endoscope image information;

a medium discriminating information imparting means for imparting medium discriminating information to said medium;

a medium controlling means for memorizing said search information and the medium discriminating information of the medium in which this search information is recorded; and a searching means for searching the medium discriminating information by inputting said search information into said medium controlling means.

2. An endoscope image filing apparatus according to claim 1 characterized in that said medium discriminating information imparting means is connected to said medium controlling means and transmits to the medium controlling means the search information and medium discriminating information recorded in the medium.

3. An endoscope image filing apparatus according to claim 1 characterized in that said recording means has an inputting means for inputting the search information.

4. An endoscope image filing apparatus according to claim 1 characterized in that said medium discriminating information imparting means and searching means are included in the same apparatus.

5. An endoscope image filing apparatus according to claim 1 characterized in that said recording means is connected to a video processor converting to a video signal the endoscope imaging signal output from the endoscope.

6. An endoscope image filing apparatus according to claim 5 characterized in that said video processor is provided with an inputting means for inputting the search information required to search the endoscope image information and transmitting it to the recording means.

7. An endoscope image filing apparatus according to claim 1 characterized in that said recording means has a controller applying an image process to the endoscope image information.

8. An endoscope image filing apparatus according to claim 7 characterized in that the image process of the controller is an image compressing process.

9. An endoscope image filing apparatus according to claim 7 characterized in that the image process of the controller is an image contracting process.

10. An endoscope image filing apparatus characterized by comprising:
- a video processor producing an endoscope video signal;
- a first recording means connected to said video processor and recording in the same medium endoscope image information and search information required to search said endoscope image information;
- an image filing means for imparting medium discriminating information !o said medium and inputting search information;
- a second recording means connected to said video processor and recording endoscope image information; and
- a medium and search information controlling means for memorizing said search information and the medium discriminating information of the medium in which this search information is recorded and for memorizing the search information required to search the endoscope image information recorded in said second recording means.

11. An endoscope image filing apparatus according to claim 10 characterized in that said second recording means is connected to a plurality of video processors connected respectively to the first recording means through a switching inputting means.

12. An endoscope image filing apparatus according to claim 10 characterized in that only one or simultaneously both of said first recording means and second recording means is or are connected with the video processor by a selecting means.

13. An endoscope image filing apparatus according to claim 10 characterized in that at least one of said second recording means and said image filing means is connected with an automatic photographing means for film-photographing the image Output by the second recording means and filing means.

14. An endoscope image filing apparatus according to claim 10 characterized in that at least one of said second recording means and image filing means is connected with a film image inputting means for obtaining image information from a film, photograph or the like.

15. An endoscope image filing apparatus according to claim 10 characterized in that said first recording means is a digital recording means for digitally recording information.

16. An endoscope image filing apparatus according to claim 10 characterized in that said first recording means is a reversibly compressing digital recording means.

17. An endoscope image filing apparatus according to claim 10 characterized in that said first recording means is an electronic camera recording in a magnetic disc image data obtained by photoelectrically converting an object image.

18. An endoscope image filing apparatus according to claim 10 characterized in that said second recording means is an analogue recording means.

19. An endoscope image filing apparatus according to claim 10 characterized in that said second recording means is a high compression digital recording means.

20. An endoscope image filing apparatus characterized in that:
- a satellite room is provided with a video processor producing an endoscope video signal and a digital image filing means connected to said video processor and digitally recording in the same medium endoscope image information and search information required to search said endoscope image information;
- a conference room is provided with a digital image filing means reproducing the endoscope image information recorded in said medium and capable of additionally recording data in said medium; and
- a control room is provided with a digital image filing means for imparting medium discriminating information to said medium and inputting search information and a medium controlling means for memorizing said search information and the medium discriminating information of the medium in which said search information is recorded.

21. An endoscope image filing apparatus according to claim 20 characterized in that said digital image filing means provided in the conference room has a medium driving means reproducing the image information recorded in the medium and capable of additionally recording information in said medium, a search information inputting means for inputting search information required to search the image information recorded in said medium, a signal processing means for signal-processing image data reproduced on the basis of the search information input from said search information inputting means and an image memory inputting and storing image data displayed in a monitor.

22. An endoscope image filing apparatus according to claim 21 characterized in that said signal processing means compresses reproduced image data.

23. An endoscope image filing apparatus according to claim 22 characterized in that said processing means for compressing image data can select a compression rate.

24. An endoscope image filing apparatus according to claim 23 characterized in that said processing means for compressing image data can alter the compression rate.

* * * * *